United States Patent
Suehiro et al.

(10) Patent No.: US 9,139,881 B2
(45) Date of Patent: Sep. 22, 2015

(54) METHOD FOR ASSESSING BREAST CANCER SUSCEPTIBILITY

(75) Inventors: Yutaka Suehiro, Ube (JP); Kohsuke Sasaki, Ube (JP); Yuji Hinoda, Ube (JP); Takae Okada, Ube (JP)

(73) Assignee: Yamaguchi University, Yamaguchi (JP)

( * ) Notice: Subject to any disclaimer, the term of this patent is extended or adjusted under 35 U.S.C. 154(b) by 5 days.

(21) Appl. No.: 13/881,030

(22) PCT Filed: Oct. 26, 2011

(86) PCT No.: PCT/JP2011/005983
§ 371 (c)(1),
(2), (4) Date: Apr. 23, 2013

(87) PCT Pub. No.: WO2012/056694
PCT Pub. Date: May 3, 2012

(65) Prior Publication Data
US 2013/0210012 A1    Aug. 15, 2013

(30) Foreign Application Priority Data
Oct. 26, 2010 (JP) ................................ 2010-240189

(51) Int. Cl.
*C12Q 1/68* (2006.01)

(52) U.S. Cl.
CPC .............. *C12Q 1/6886* (2013.01); *C12Q 1/686* (2013.01); *C12Q 2600/112* (2013.01); *C12Q 2600/156* (2013.01)

(58) Field of Classification Search
None
See application file for complete search history.

(56) References Cited

FOREIGN PATENT DOCUMENTS

| JP | 2003-043046 | 2/2003 |
|----|-------------|--------|
| JP | 2008-048668 | 3/2008 |
| JP | 2008-092949 | 4/2008 |
| JP | 2008-531041 | 8/2008 |
| WO | WO 2006/095985 | 9/2006 |

OTHER PUBLICATIONS

Roche NibleGen Human CGH HD2 Array product sheet, 2008, available via url: <roche-biochem.jp/pdf/products/microarray/user_guide/CGH/CGH_HD2_datasheet.pdf>.*
The Meriam Webster Dictionary definition for "Detect," printed on May 20, 2014, available via url: <merriam-webster.com/dictionary/detect>.*
Hwang et al. Int J Cancer. 2008. 123: 1807-1815.*
Prat et al. Nature. Scientific Reports. Dec. 18, 2013. 2:2544, p. 1-12.*
Klopocki et al Annual Reviews Genomics Human Genetics. 2011. 12: 53-72.*
Al-Mulla et al. J Clin Pathol: Mol Pathol. 2003. 56: 210-217.*
Kawauchi et al. International J Mol Medicine. 2010. 26: 333-339.*
Osterberg, L. (Doctoral Thesis. Characterization of Genetic Alterations in Ovarian Cancer Associated with Chemotherapy Response. 2009. Dept. Oncology. The Sahlgrenska Academy at University of Gothenburg, Gotherburg Sweden, Intellecta Infolog AB.*
Tanaka et al., "Indentification of High Risk Carriers of Breast or Ovary Cancer by Functional Analysis of Gene Instability and Construction of Models for Predicting Gene Mutation, and Establishment of the Onset-Preventing Method, " Health and Labour Sciences Research Grant (3$^{rd}$ Term Comprehensive Cancer Control Strategy) dated May 2010, 40 pages.
Tchatchou et al., "Chromosome Copy Number Variation and Breast Cancer Risk, " Cytogenic and Genome Research, 2008 vol. 123, p. 183-7.
Lee et al., "Genome-Wide Copy Number Variation and Breast Cancer risk: Preliminary Report," Cancer Research, Apr. 15, 2010 70;4720. (Abstract Only).
Frank et al., "Copy Number Variant in the Candidate Tumor Suppressor Gene MTUS1 and Familial Breast Cancer Risk," Carcinogenesis vol. 28, No. 7, pp. 1442-1445, 2007.

* cited by examiner

*Primary Examiner* — Carla Myers
(74) *Attorney, Agent, or Firm* — Cadwalader Wickersham & Taft LLP

(57) ABSTRACT

The present invention aims to provide a method for determining breast cancer susceptibility, in which a DNA copy number polymorphism associated with breast cancer susceptibility is identified and determination is made based on an increase or decrease in the DNA copy number polymorphism. The present invention attempts to achieve this by performing microarray assay using the peripheral blood of sporadic breast cancer patients, identifying a DNA copy number polymorphism associated with breast cancer susceptibility in a chromosomal region, detecting the number of copies of the above DNA copy number polymorphism by quantitative PCR, and then determining breast cancer susceptibility based on an increase or decrease in the DNA copy number polymorphism. Furthermore, the precision of the determination of breast cancer susceptibility can be improved by detecting a DNA copy number polymorphism by the aforementioned quantitative PCR by selecting two or more chromosomal regions and then performing a discriminant analysis based on the results thus obtained.

2 Claims, 29 Drawing Sheets

DISCRIMINANT FORMULA =Hs06535529_cn COPY No.×(-0.5695)+Hs04093415_cn COPY No.×(0.0236)+(0.7142)

DISCRIMINANT SCORE OF 0 OR MORE
= SUSCEPTIBLE TO BREAST CANCER

DISCRIMINANT SCORE OF LESS THAN 0
= NOT SUSCEPTIBLE TO BREAST

SENSITIVITY 82.4%, SPECIFICITY 51.9%

DISCRIMINANT FORMULA =Hs06535529_cn COPY No.× (0.1403)+Hs03899300_cn COPY No.× (-2.9466)+(4.2074)

DISCRIMINANT SCORE OF 0 OR MORE
= SUSCEPTIBLE TO BREAST CANCER

DISCRIMINANT SCORE OF LESS THAN 0
= NOT SUSCEPTIBLE TO BREAST

| | | DISCRIMINATED GROUP | | |
| --- | --- | --- | --- | --- |
| | | BREAST CANCER | CONTROL | TOTAL |
| TRUE GROUP | BREAST CANCER | 142 | 51 | 193 |
| | CONTROL | 53 | 163 | 216 |

SENSITIVITY 73.6%, SPECIFICITY 75.5%

DISCRIMINANT FORMULA =Hs06535529_cn COPY No×(0.1399)+Hs03898338_cn COPY No×(−3.7991)+(5.2721)

DISCRIMINANT SCORE OF 0 OR MORE
= SUSCEPTIBLE TO BREAST CANCER
DISCRIMINANT SCORE OF LESS THAN 0
= NOT SUSCEPTIBLE TO BREAST

|  |  | DISCRIMINATED GROUP | | |
|---|---|---|---|---|
|  |  | BREAST CANCER | CONTROL | TOTAL |
| TRUE GROUP | BREAST CANCER | 152 | 41 | 193 |
|  | CONTROL | 54 | 162 | 216 |

SENSITIVITY 78.8%, SPECIFICITY 75.0%

DISCRIMINANT FORMULA =Hs06535529_cn COPY No×(−0.3911)+Hs03908783_cn COPY No×(−0.3972)+(1.0298)

DISCRIMINANT SCORE OF 0 OR MORE
= SUSCEPTIBLE TO BREAST CANCER

DISCRIMINANT SCORE OF LESS THAN 0
= NOT SUSCEPTIBLE TO BREAST

| | | DISCRIMINATED GROUP | | |
| --- | --- | --- | --- | --- |
| | | BREAST CANCER | CONTROL | TOTAL |
| TRUE GROUP | BREAST CANCER | 154 | 39 | 193 |
| | CONTROL | 97 | 119 | 216 |

SENSITIVITY 79.8%, SPECIFICITY 55.1%

DISCRIMINANT FORMULA =Hs04093415_cn COPY No.×(-0.2285)+Hs04090898_cn COPY No.×(0.1834)+(-0.0272)

DISCRIMINANT SCORE OF 0 OR MORE
= SUSCEPTIBLE TO BREAST CANCER

DISCRIMINANT SCORE OF LESS THAN 0
= NOT SUSCEPTIBLE TO BREAST

| | | DISCRIMINATED GROUP | | |
|---|---|---|---|---|
| | | BREAST CANCER | CONTROL | TOTAL |
| TRUE GROUP | BREAST CANCER | 35 | 158 | 193 |
| | CONTROL | 32 | 184 | 216 |

SENSITIVITY 18.1%, SPECIFICITY 85.2%

DISCRIMINANT FORMULA = Hs04093415_cn COPY No.×(0.0316)+Hs03908783_cn COPY No.×(−0.9415)+(1.1523)

DISCRIMINANT SCORE OF 0 OR MORE
= SUSCEPTIBLE TO BREAST CANCER

DISCRIMINANT SCORE OF LESS THAN 0
= NOT SUSCEPTIBLE TO BREAST

| | | DISCRIMINATED GROUP | | |
|---|---|---|---|---|
| | | BREAST CANCER | CONTROL | TOTAL |
| TRUE GROUP | BREAST CANCER | 138 | 55 | 193 |
| | CONTROL | 86 | 130 | 216 |

SENSITIVITY 71.5%, SPECIFICITY 60.2%

DISTRIBUTION OF DISCRIMINANT SCORE

DISCRIMINANT FORMULA =Hs04093415_cnCOPY No.×(0.005)+Hs03103056_cnCOPY No.×(0.5142)+(-1.3547)

DISCRIMINANT SCORE OF 0 OR MORE
= SUSCEPTIBLE TO BREAST CANCER

DISCRIMINANT SCORE OF LESS THAN 0
= NOT SUSCEPTIBLE TO BREAST

| | | DISCRIMINATED GROUP | | |
|---|---|---|---|---|
| | | BREAST CANCER | CONTROL | TOTAL |
| TRUE GROUP | BREAST CANCER | 118 | 75 | 193 |
| | CONTROL | 103 | 113 | 216 |

SENSITIVITY 61.1%, SPECIFICITY 52.3%

DISCRIMINANT FORMULA =Hs04090898_cn COPY No.×(0.0385)+Hs03899300_cn COPY No.×(-2.6967)+(3.9289)

DISCRIMINANT SCORE OF 0 OR MORE
= SUSCEPTIBLE TO BREAST CANCER

DISCRIMINANT SCORE OF LESS THAN 0
= NOT SUSCEPTIBLE TO BREAST

| | | DISCRIMINATED GROUP | | |
|---|---|---|---|---|
| | | BREAST CANCER | CONTROL | TOTAL |
| TRUE GROUP | BREAST CANCER | 146 | 47 | 193 |
| | CONTROL | 55 | 161 | 216 |

SENSITIVITY 75.7%, SPECIFICITY 74.5%

DISCRIMINANT FORMULA =Hs04090898_cn COPY No×(0.031)+Hs03908783_cn COPY No×(-0.943)+(1.137)

DISCRIMINANT SCORE OF 0 OR MORE
= SUSCEPTIBLE TO BREAST CANCER

DISCRIMINANT SCORE OF LESS THAN 0
= NOT SUSCEPTIBLE TO BREAST

| | | DISCRIMINATED GROUP | | |
|---|---|---|---|---|
| | | BREAST CANCER | CONTROL | TOTAL |
| TRUE GROUP | BREAST CANCER | 139 | 54 | 193 |
| | CONTROL | 86 | 130 | 216 |

SENSITIVITY 72.0%, SPECIFICITY 60.2%

DISCRIMINANT FORMULA =Hs04090898_cn COPY No.×(0.0191)+Hs03898338_cn COPY No.×(-3.5282)+(5.0233)

DISCRIMINANT SCORE OF 0 OR MORE
= SUSCEPTIBLE TO BREAST CANCER

DISCRIMINANT SCORE OF LESS THAN 0
= NOT SUSCEPTIBLE TO BREAST

| | | DISCRIMINATED GROUP | | |
|---|---|---|---|---|
| | | BREAST CANCER | CONTROL | TOTAL |
| TRUE GROUP | BREAST CANCER | 152 | 41 | 193 |
| | CONTROL | 54 | 162 | 216 |

SENSITIVITY 78.8%, SPECIFICITY 75.0%

DISCRIMINANT FORMULA =Hs03899300_cnCOPY No.×(−0.6719)+Hs03898338_cnCOPY No.×(−2.929)+(5.2098)

DISCRIMINANT SCORE OF 0 OR MORE
= SUSCEPTIBLE TO BREAST CANCER

DISCRIMINANT SCORE OF LESS THAN 0
= NOT SUSCEPTIBLE TO BREAST

| | | DISCRIMINATED GROUP | | |
|---|---|---|---|---|
| | | BREAST CANCER | CONTROL | TOTAL |
| TRUE GROUP | BREAST CANCER | 154 | 39 | 193 |
| | CONTROL | 52 | 164 | 216 |

SENSITIVITY 79.8%, SPECIFICITY 75.9%

DISCRIMINANT FORMULA =Hs03899300_cn COPY No.×(-3.0532)+Hs03103056_cn COPY No.×(0.7876)+(2.4915)

DISCRIMINANT SCORE OF 0 OR MORE
= SUSCEPTIBLE TO BREAST CANCER

DISCRIMINANT SCORE OF LESS THAN 0
= NOT SUSCEPTIBLE TO BREAST

| | | DISCRIMINATED GROUP | | |
|---|---|---|---|---|
| | | BREAST CANCER | CONTROL | TOTAL |
| TRUE GROUP | BREAST CANCER | 153 | 40 | 193 |
| | CONTROL | 54 | 162 | 216 |

SENSITIVITY 79.3%, SPECIFICITY 75.0%

DISCRIMINANT FORMULA =Hs03908783_cn COPY No×(0.7877)+Hs03898338_cn COPY No×(-4.5371)+(5.5065)

DISCRIMINANT SCORE OF 0 OR MORE
= SUSCEPTIBLE TO BREAST CANCER

DISCRIMINANT SCORE OF LESS THAN 0
= NOT SUSCEPTIBLE TO BREAST

|  |  | DISCRIMINATED GROUP | | |
|---|---|---|---|---|
|  |  | BREAST CANCER | CONTROL | TOTAL |
| TRUE GROUP | BREAST CANCER | 163 | 30 | 193 |
|  | CONTROL | 53 | 163 | 216 |

SENSITIVITY 84.5%, SPECIFICITY 75.5%

METHOD FOR ASSESSING BREAST CANCER SUSCEPTIBILITY

TECHNICAL FIELD

The present invention relates to a method and a kit for determining breast cancer susceptibility by detecting a DNA copy number polymorphism in human chromosomal regions.

BACKGROUND ART

In Japan, cancer is the leading cause of death. Therefore, cancer control is the highest priority issue from the viewpoint of national health. A basic solution for reducing mortality from cancer is to avoid developing cancer, and "prevention of cancer development and early detection of cancer" are regarded as important. However, because a method for determining cancer susceptibility (a predisposition to cancer) has not yet been fully established, diagnosis and treatment are more focused on early detection (secondary prevention) than on the prevention of cancer development (primary prevention) under the present circumstances. In light of the above, if susceptibility to various types of cancer can be determined in each individual in advance, prevention of cancer development, including improving "lifestyles and living environments" etc., can be effectively accomplished, and not only that, current cancer screening will be efficiently and effectively carried out, hopefully increasing the consultation rate.

Also with regard to breast cancer, several methods for determining the degree of progression of the disease and the risk of developing the disease have been proposed. For example, a method for determining breast cancer, characterized by confirming the presence or absence of the endothelial protein C receptor (EPCR) in a biological sample and determining the subject as positive based on the presence of the above substance has been proposed (see for example, Patent Document 1). This method can be used for the detection of a breast cancer cell, which might be overlooked when only cellular and nuclear morphology is observed; for the detection of a breast cancer cell in the lymph nodes for determination of the degree of lymph node dissection in surgery; and for similar assessment and treatment after metastasis. Also, a method for diagnosing breast cancer in subjects aged 40 years or younger or 55 years or older, comprising the step of obtaining a nucleic acid from a subject and determining a nucleotide at a polymorphic site in the nucleic acid (see for example, Patent Document 2) has been proposed. Further, a method for diagnosing breast cancer or a predisposing factor to develop breast cancer in a subject, comprising the step of determining the expression level of a breast cancer-associated gene in a biological sample derived from a patient and assessing the subject as having breast cancer or a risk of developing breast cancer when the expression level in the sample is increased or decreased in comparison with the level of the gene in a normal control (see for example, Patent Document 3) has been proposed.

A DNA copy number polymorphism (CNP) was reported in 2004 as a condition in which DNA duplication or deletion of as many as about 100 kb in size occurs in a specific chromosomal region. In 2008, it was reported that DNA copy number polymorphisms were present in about 20,000 sites in human genome. A DNA copy number polymorphism is a phenomenon in which the number of copies of several thousand base pairs to several million base pairs varies from one individual to another. Normally, human genes are inherited in two copies in total, one copy from the maternal genome and the other copy from the paternal genome. However, it is known that genes are present in only one copy or three or more copies per cell depending on the individual due to DNA copy number polymorphism in the gene region. As a cause of generating constitutional differences among individuals as observed in various degrees of sensitivity to drugs and various levels of manifestation of side effects, "variation in the nucleotide sequence" of human genes has been widely known as represented by Single Nucleotide Polymorphism (SNP). Also, recently, DNA copy number polymorphism has been receiving increasing attention from the aspect of "variation in the number" of genes.

The present inventors have reported a method for determining endometrial cancer susceptibility and colorectal cancer susceptibility using DNA copy number polymorphism as an index (see Patent Document 4). However, DNA copy number polymorphism enabling determination of breast cancer susceptibility has not hitherto been known.

PRIOR ART DOCUMENTS

Patent Documents

Patent Document 1: Japanese unexamined Patent Application Publication No. 2003-43046
Patent Document 2: Japanese unexamined Patent Application Publication (Translation of PCT Application) No. 2008-531041
Patent Document 3: Japanese unexamined Patent Application Publication No. 2008-92949
Patent Document 4: Japanese unexamined Patent Application Publication No. 2008-48668

SUMMARY OF THE INVENTION

Object to be Solved by the Invention

It is known that the risk of developing breast cancer can be reduced by improving lifestyles, and regular check-up enables early detection and early treatment, thereby decreasing mortality from cancer. Therefore, if breast cancer susceptibility can be determined, people are expected to be strongly motivated to act in such a way as to reduce the risk of developing breast cancer (practicing physical activities such as sport, being careful not to get fat, and reducing the amount of drinking) and actually act in such a way, and public awareness is expected to increase, encouraging people to actively receive cancer screening. As a result, cancer prevention can be achieved, and even if one develops cancer, early detection and early treatment can be provided, which could greatly reduce mortality from cancer. Among the types of breast cancer, the BRCA1 and BRCA2 genes are known to be used for the prediction of the risk of hereditary breast cancer. However, for sporadic breast cancer other than hereditary breast cancer, a DNA region that can be used for highly precise prediction of the risk of developing cancer has not yet been discovered. An object of the present invention is to identify a DNA copy number polymorphism associated with breast cancer susceptibility and provide a method for determining breast cancer susceptibility based on the increase or decrease of the DNA copy number polymorphism.

Means to Solve the Object

The present inventors identified, for the first time in the world, a DNA copy number polymorphism characteristic of breast cancer patients by microarray assay using DNA derived from the peripheral blood. Subsequently, in attempting to verify a predisposition to breast cancer based on the increase or decrease in DNA copy number polymorphic regions simply at low cost with high precision, the inventors performed quantitative PCR analysis. By quantitative PCR, the present inventors have specifically detected a specific region within the chromosomal region identified by microarray assay. That is, the present inventors have detected a smaller chromosomal region than that identified by microarray assay. Further, based on the possibility that both sensitivity and specificity can be improved by using a combination of a plurality of CNP regions relative to a single CNP region, the inventors also attempted to predict a predisposition to breast cancer by using a combination of a plurality of CNPs.

The present inventors verified the relevance to a predisposition to breast cancer by performing quantitative PCR using six times or more than six times greater number of samples than the number of samples used in the microarray assay. As a result, for example, a frequency of decrease in DNA copy number (a copy number of less than 1.5) in the chromosomal region (15q26.3 [99,845,920 to 99,846,025]) as detected with the primer set (Hs03899300_cn) was found to be 25.9% in the group of healthy individuals, whereas that was found to be 76.7% in the group of breast cancer patients with an odds ratio of 9.4. That is, it was found that when there is a decrease in DNA copy number in this region, an individual is prone to breast cancer. Similarly, a frequency of decrease in DNA copy number (a copy number of less than 0.5) in the chromosomal region (15q26.3 [99,847,947 to 99,848,043]) as detected with the primer set (Hs03908783_cn) was found to be 10.2% in the group of healthy individuals, whereas that was found to be 23.8% in the group of breast cancer patients with an odds ratio of 2.8. That is, it was found that when there is a decrease in DNA copy number in this region, an individual is prone to breast cancer. Further, as a result of a discriminant analysis based on the results of quantitative PCR of the above two regions, the percentage of determination as "having breast cancer" in the group of breast cancer patients was found to be 83.9% (sensitivity), while the percentage of determination as "not having breast cancer" in the group of healthy individuals was found to be 81.0% (specificity). That is, the present inventors have found a high precision method for determining breast cancer susceptibility, thereby completing the present invention.

That is, the present invention relates to (1) a method for determining breast cancer susceptibility, comprising detecting at least one DNA copy number polymorphism in human chromosomal regions listed in the following [Group A]:
[Group A]
1q44 (246,855,947-246,857,101)
1q44 (246,857,101-246,858,266)
1p36.12 (21,373,559-21,374,437)
1p36.12 (21, 374, 437-21, 376, 929)
1p36.12 (21,376,929-21,378,068)
2p16.3 (52,603,488-52,605,502)
2p16.3 (52,605,502-52,606,645)
2p16.3 (52,606,645-52,611,965)
2p16.3 (52,611,965-52,620,153)
2p16.3 (52,620,153-52,622,543)
2p16.3 (52,622,543-52,636,901)
2p16.3 (52,636,901-52,638,223)
2q24.3 (165,544,576-165,563,420)
2p16.3 (52,606,645-52,625,528)
2p16.3 (52,625,528-52,634,972)
2p16.3 (52,636,079-52,636,901)
3q26.1 (163,701,862-163,705,223)
3q26.1 (163,698,399-163,714,957)
3q26.1 (163,714,957-163,716,880)
3q26.1 (163,716, 880-163,718,292)
6p25.3 (256,364-307,220)
6p25.3 (307,220-324,877)
7q31.1 (109,240,145-109,241,260)
7p13 (43,968,813-43,969,989)
7p13 (43,969,989-43,973,917)
7p13 (44,033,292-44,046,944)
7p13 (44,965,401-44,966,288)
8p23.1 (7,331,151-7,366,894)
8p23.1 (7,384,482-7,385,717)
8p23.1 (7,385,717-7,675,644)
8p23.1 (7,675,644-7,677,003)
8p23.1 (7,729,310-7,756,222)
8p23.1 (7,766,308-7,785,964)
8p23.1 (7,789,316-7,796,881)
8p23.1 (7,796,881-7,804,843)
8p23.1 (7,804,843-7,812,725)
8p11.23-p11.22 (39,351,598-39,352,968)
8p11.23-p11.22 (39,352,968-39,505,316)
8p11.23-p11.22 (39,505,316-39,506,703)
9p11.2 (43,752,248-43,754,446)
9q12-q13 (69,950,626-70,000,416)
9q12-q13 (70,000,416-70,026,246)
10p12.31 (22,644,992-22,646,132)
10p12.31 (22,646,132-22,647,050)
10p12.31 (22,648,356-22,654,917)
10p12.31 (22,654,917-22,656,057)
10q21.3 (66,977,059-66,982,379)
11q13.1 (64,298,883-64,299,791)
11q13.1 (64,299,791-64,300,705)
11q13.1 (64,300,705-64,303,775)
11q13.1 (64,303,775-64,305,075)
11q13.1 (64,305,075-64,309,752)
11q13.1 (64,309,752-64,310,507)
15q11.2 (19,054,967-19,055,863)
15q11.2 (20,081,406-20,091,581)
15q11.2 (20,091,581-20,146,200)
15q25.2 (80,700,012-80,703,055)
15q25.2 (80,703,055-80,704,239)
15q26.3 (99, 847, 229-99, 848, 361)
15q26.3 (99, 848, 361-99, 851, 910)
16p13.3 (1,374,245-1,386,928)
16p13.3 (1,409,635-1,451,145)
16p13.3 (2,530,856-2,531,917)
16p13.3 (4,688,278-4,689,410)
16p12.1 (22,587,790-22,590,317)
16p12.1 (22,602,200-22,605,904)
16p12.1 (22,605,904-22,610,525)
16p12.1 (22,612,746-22,614,711)
17p11.2 (18,864,114-18,866,684)
17q12 (33,593,624-33,606,100)
17q21.31 (39,786,143-39,789,781)
17q21.31 (39,789,781-39,791,475)
19q13.33 (55,769,626-55,774,306)
19q13.42 (60,579,276-60,581,130)
19q13.42 (60,581,130-60,582,666)
19q13.42 (60,582,666-60,588,237)
19q13.42 (60,588,237-60,589,160)
19q13.42 (60,589,160-60,589,969)
19q13.42 (60,597,122-60,598,638)
19q13.42 (60,598,638-60,599,772)
19q13.42 (60,599,772-60,601,009)
22q11.1 (14,529,177-14,551,306)
22q12.3 (35,474,202-35,477,701)
22q11.21 (18,698,449-18,701,734)
22q11.21 (18,708,863-18,718,104)
22q11.21 (18,744,485-18,751,648)

22q11.21 (18,751,648-18,757,015)
22q11.21 (18,763,247-18,764,375)
22q11.21 (18,764,375-18,766,608)
22q11.21 (18,766,608-18,767,909)
22q11.21 (18,767,909-18,803,304)
22q11.21 (18,851,650-18,854,853)
22q11.21 (18,861,035-18,862,757)
22q11.21 (20,129,733-20,132,553)
22q11.21 (20,139,367-20,140,478)
22q11.21 (20,142,316-20,143,929)
22q11.21 (20,157,427-20,158,507)
22q11.21 (20,158,507-20,163,759)
22q11.21 (20,163,759-20,166,938)
22q11.21 (20,166,938-20,189,915)
22q11.21 (20,189,915-20,194,583)
22q11.21 (20,194,583-20,198,780)
22q11.21 (20,198,780-20,206,030)
22q11.21 (20,206,030-20,233,462)
22q11.21 (20,233,462-20,239,367)
22q11.21 (20,239,367-20,243,220)
22q11.21 (20,243,220-20,244,301)
22q12.3 (35,472,904-35,474,202)
Xq26.3 (134,686,768-134,710,721)
Xq26.3 (134,715,826-134,718,277)

The present invention also relates to (2) the determination method according to the aforementioned (1), wherein the DNA copy number polymorphism is detected by microarray assay, and also to (3) a method for determining breast cancer susceptibility, comprising detecting a decrease of at least one DNA copy number in human chromosomal regions listed in the following [Group B] and/or an increase of at least one DNA copy number in human chromosomal regions listed in the following [Group C]:

[Group B]
1p36.12 (21,375,430-21,375,511) consisting of the nucleotide sequence shown in SEQ ID NO: 1,
15q26.3 (99,845,920-99,846,025) consisting of the nucleotide sequence shown in SEQ ID NO: 3,
15q26.3 (99,847,947-99,848,043) consisting of the nucleotide sequence shown in SEQ ID NO: 4, and
15q26.3 (99,848,547-99,848,623) consisting of the nucleotide sequence shown in SEQ ID NO: 5,

[Group C]
3q26.1 (163,706,172-163,706,287) consisting of the nucleotide sequence shown in SEQ ID NO: 2,
22q12.3 (35,473,730-35,473,804) consisting of the nucleotide sequence shown in SEQ ID NO: 6, and
22q12.3 (35,475,937-35,476,043) consisting of the nucleotide sequence shown in SEQ ID NO: 7.

The present invention further relates to (4) the determination method according to the aforementioned (3), comprising performing a discriminant analysis by selecting two or more from [Group B] and/or [Group C], (5) the determination method according to the aforementioned (4), comprising selecting 15q26.3 (99,845,920-99,846,025) consisting of the nucleotide sequence shown in SEQ ID NO: and 15q26.3 [99,847,947-99,848,043] consisting of the nucleotide sequence shown in SEQ ID NO: 4, and (6) the determination method according to any one of the aforementioned (3) to (5), comprising detecting a DNA copy number by quantitative PCR.

Other aspects of the present invention include a method for collecting data for the determination of breast cancer susceptibility and a method for collecting data for the prediction of the prognosis of breast cancer treatment.

The present invention also relates to (7) a kit for determining breast cancer susceptibility, comprising a primer set or probe, or a labeled primer set or probe for the detection of at least one DNA copy number polymorphism in human chromosomal regions listed in the following [Group A]:

[Group A]
1q44 (246,855,947-246,857,101)
1q44 (246,857,101-246,858,266)
1p36.12 (21,373,559-21,374,437)
1p36.12 (21, 374, 437-21, 376, 929)
1p36.12 (21,376,929-21,378,068)
2p16.3 (52,603,488-52,605,502)
2p16.3 (52,605,502-52,606,645)
2p16.3 (52,606,645-52,611,965)
2p16.3 (52,611,965-52,620,153)
2p16.3 (52,620,153-52,622,543)
2p16.3 (52,622,543-52,636,901)
2p16.3 (52,636,901-52,638,223)
2q24.3 (165,544,576-165,563,420)
2p16.3 (52,606,645-52,625,528)
2p16.3 (52,625,528-52,634,972)
2p16.3 (52,636,079-52,636,901)
3q26.1 (163,701,862-163,705,223)
3q26.1 (163,698,399-163,714,957)
3q26.1 (163,714,957-163,716,880)
3q26.1 (163,716,880-163,718,292)
6p25.3 (256,364-307,220)
6p25.3 (307,220-324,877)
7q31.1 (109,240,145-109,241,260)
7p13 (43,968,813-43,969,989)
7p13 (43,969,989-43,973,917)
7p13 (44,033,292-44,046,944)
7p13 (44,965,401-44,966,288)
8p23.1 (7,331,151-7,366,894)
8p23.1 (7,384,482-7,385,717)
8p23.1 (7,385,717-7,675,644)
8p23.1 (7,675,644-7,677,003)
8p23.1 (7,729,310-7,756,222)
8p23.1 (7,766,308-7,785,964)
8p23.1 (7,789,316-7,796,881)
8p23.1 (7,796,881-7,804,843)
8p23.1 (7,804,843-7,812,725)
8p11.23-p11.22 (39,351,598-39,352,968)
8p11.23-p11.22 (39,352,968-39,505,316)
8p11.23-p11.22 (39,505,316-39,506,703)
9p11.2 (43,752,248-43,754,446)
9q12-q13 (69,950,626-70,000,416)
9q12-q13 (70,000,416-70,026,246)
10p12.31 (22,644,992-22,646,132)
10p12.31 (22,646,132-22,647,050)
10p12.31 (22,648,356-22,654,917)
10p12.31 (22,654,917-22,656,057)
10q21.3 (66,977,059-66,982,379)
11q13.1 (64,298,883-64,299,791)
11q13.1 (64,299,791-64,300,705)
11q13.1 (64,300,705-64,303,775)
11q13.1 (64,303,775-64,305,075)
11q13.1 (64,305,075-64,309,752)
11q13.1 (64,309,752-64,310,507)
15q11.2 (19,054,967-19,055,863)
15q11.2 (20,081,406-20,091,581)
15q11.2 (20,091,581-20,146,200)
15q25.2 (80,700,012-80,703,055)
15q25.2 (80,703,055-80,704,239)
15q26.3 (99,847,229-99,848,361)
15q26.3 (99,848,361-99,851,910)
16p13.3 (1,374,245-1,386,928)
16p13.3 (1,409,635-1,451,145)
16p13.3 (2,530,856-2,531,917)

16p13.3 (4,688,278-4,689,410)
16p12.1 (22,587,790-22,590,317)
16p12.1 (22,602,200-22,605,904)
16p12.1 (22,605,904-22,610,525)
16p12.1 (22,612,746-22,614,711)
17p11.2 (18,864,114-18,866,684)
17q12 (33,593,624-33,606,100)
17q21.31 (39,786,143-39,789,781)
17q21.31 (39,789,781-39,791,475)
19q13.33 (55,769,626-55,774,306)
19q13.42 (60,579,276-60,581,130)
19q13.42 (60,581,130-60,582,666)
19q13.42 (60,582,666-60,588,237)
19q13.42 (60,588,237-60,589,160)
19q13.42 (60,589,160-60,589,969)
19q13.42 (60,597,122-60,598,638)
19q13.42 (60,598,638-60,599,772)
19q13.42 (60,599,772-60,601,009)
22q11.1 (14,529,177-14,551,306)
22q12.3 (35,474,202-35,477,701)
22q11.21 (18,698,449-18,701,734)
22q11.21 (18,708,863-18,718,104)
22q11.21 (18,744,485-18,751,648)
22q11.21 (18,751,648-18,757,015)
22q11.21 (18,763,247-18,764,375)
22q11.21 (18,764,375-18,766,608)
22q11.21 (18,766,608-18,767,909)
22q11.21 (18,767,909-18,803,304)
22q11.21 (18,851,650-18,854,853)
22q11.21 (18,861,035-18,862,757)
22q11.21 (20,129,733-20,132,553)
22q11.21 (20,139,367-20,140,478)
22q11.21 (20,142,316-20,143,929)
22q11.21 (20,157,427-20,158,507)
22q11.21 (20,158,507-20,163,759)
22q11.21 (20,163,759-20,166,938)
22q11.21 (20,166,938-20,189,915)
22q11.21 (20,189,915-20,194,583)
22q11.21 (20,194,583-20,198,780)
22q11.21 (20,198,780-20,206,030)
22q11.21 (20,206,030-20,233,462)
22q11.21 (20,233,462-20,239,367)
22q11.21 (20,239,367-20,243,220)
22q11.21 (20,243,220-20,244,301)
22q12.3 (35,472,904-35,474,202)
Xq26.3 (134,686,768-134,710,721)
Xq26.3 (134,715,826-134,718,277)

The present invention also relates to (8) a kit for determining breast cancer susceptibility, comprising a primer set or probe, or a labeled primer set or probe for the detection of at least one DNA copy number polymorphism in human chromosomal regions listed in the following [Group B] and/or [Group C]:

[Group B]
1p36.12 (21,375,430-21,375,511) consisting of the nucleotide sequence shown in SEQ ID NO: 1,
15q26.3 (99,845,920-99,846,025) consisting of the nucleotide sequence shown in SEQ ID NO: 3,
15q26.3 (99,847,947-99,848,043) consisting of the nucleotide sequence shown in SEQ ID NO: 4, and
15q26.3 (99,848,547-99,848,623) consisting of the nucleotide sequence shown in SEQ ID NO: 5,

[Group C]
3q26.1 (163,706,172-163,706,287) consisting of the nucleotide sequence shown in SEQ ID NO: 2,
22q12.3 (35,473,730-35,473,804) consisting of the nucleotide sequence shown in SEQ ID NO: 6, and
22q12.3 (35,475,937-35,476,043) consisting of the nucleotide sequence shown in SEQ ID NO: 7.

Effect of the Invention

The present invention enables determination of a predisposition to breast cancer (breast cancer susceptibility [risk of developing breast cancer]) using a normal tissue such as blood, which is easily obtainable, as a material. As a result, the number of individuals who receive cancer screening such as a regular medical check-up, which is necessary for the prevention of disease development and early detection, is expected to increase, and moreover, the number of individuals who receive screening and are given diagnosis and treatment at an early stage of cancer will be increased, and the determination of sporadic breast cancer, the prediction of which has heretofore been deemed impossible, will become possible, whereby mortality from breast cancer is expected to decrease.

MODE OF CARRYING OUT THE INVENTION

Figure 1:
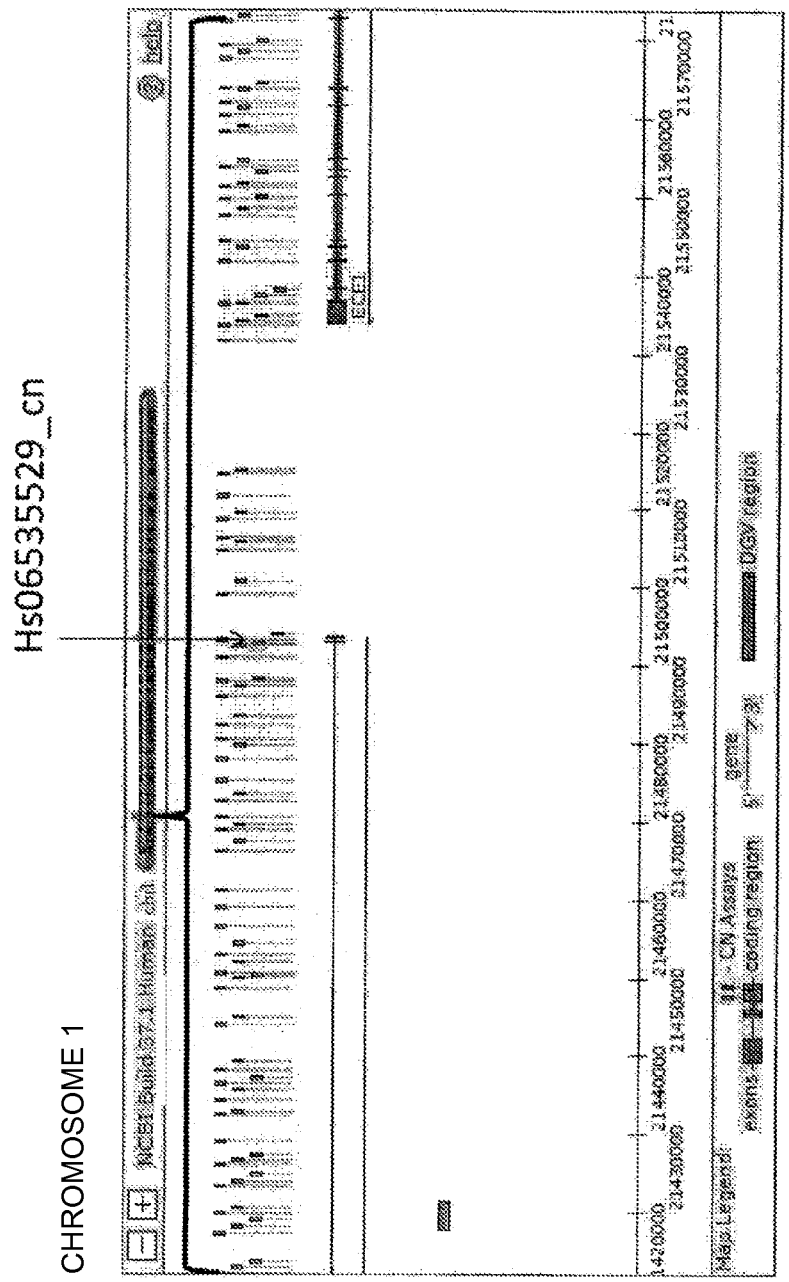
FIG. 1 is a diagram showing the chromosomal region of the DNA copy number polymorphism associated with breast cancer susceptibility detected by quantitative PCR with the primer set (Hs06535529_cn) in the chromosome 1p36.12 based on the human chromosome location information provided in "NCBI; February 2009 human reference sequence (Build 37.1)".
Figure 2:
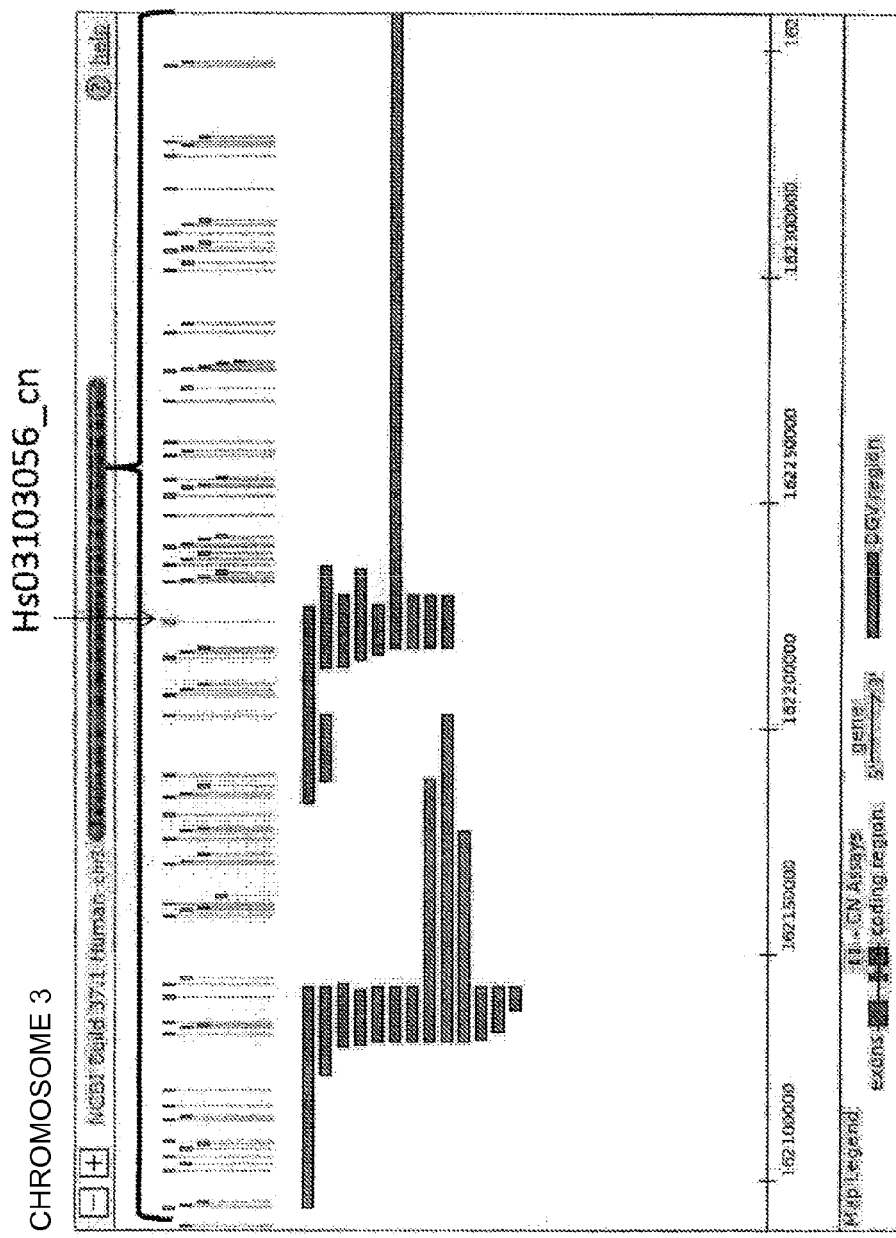
FIG. 2 is a diagram showing the chromosomal region of the DNA copy number polymorphism associated with breast cancer susceptibility detected by quantitative PCR with the primer set (Hs03103056_cn) in the chromosome 3q26.1 based on the human chromosome location information provided in "NCBI; February 2009 human reference sequence (Build 37.1)".
Figure 3:
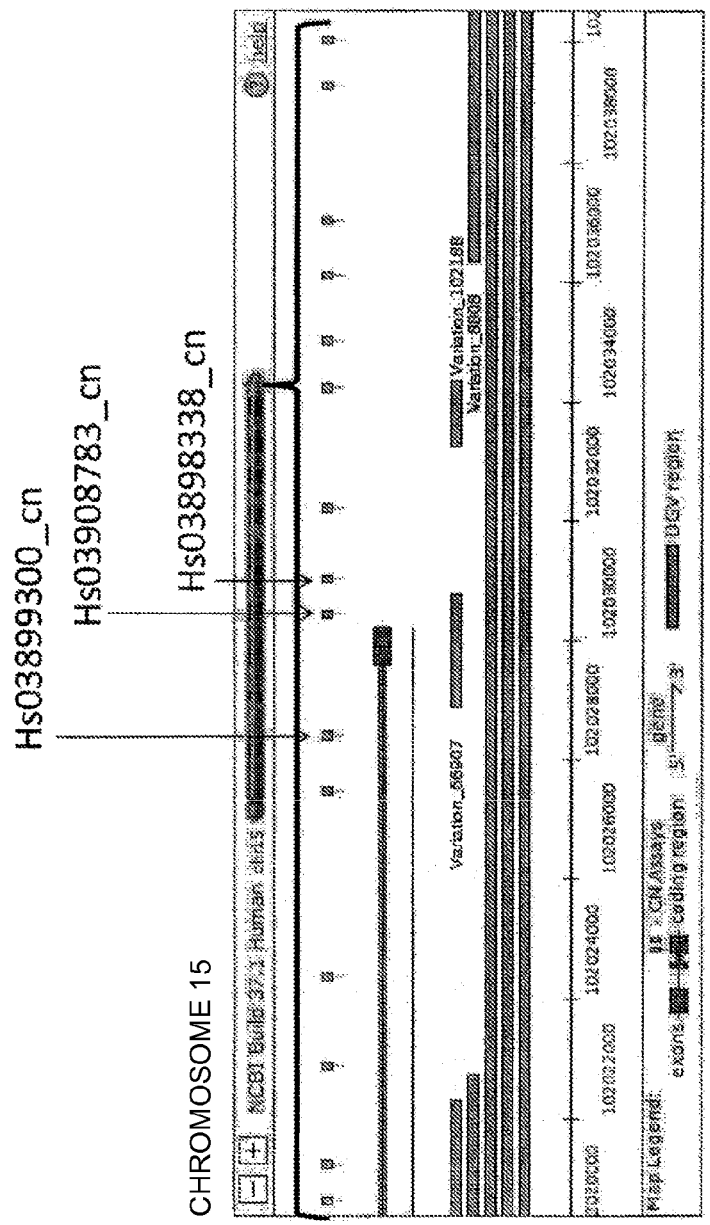
FIG. 3 is a diagram showing the chromosomal region of the DNA copy number polymorphism associated with breast cancer susceptibility detected by quantitative PCR with the primer set (Hs03899300_cn, Hs03908783_cn, or Hs03898388_cn) in the chromosome 15q26.3 based on the human chromosome location information provided in "NCBI; February 2009 human reference sequence (Build 37.1)".
Figure 4:
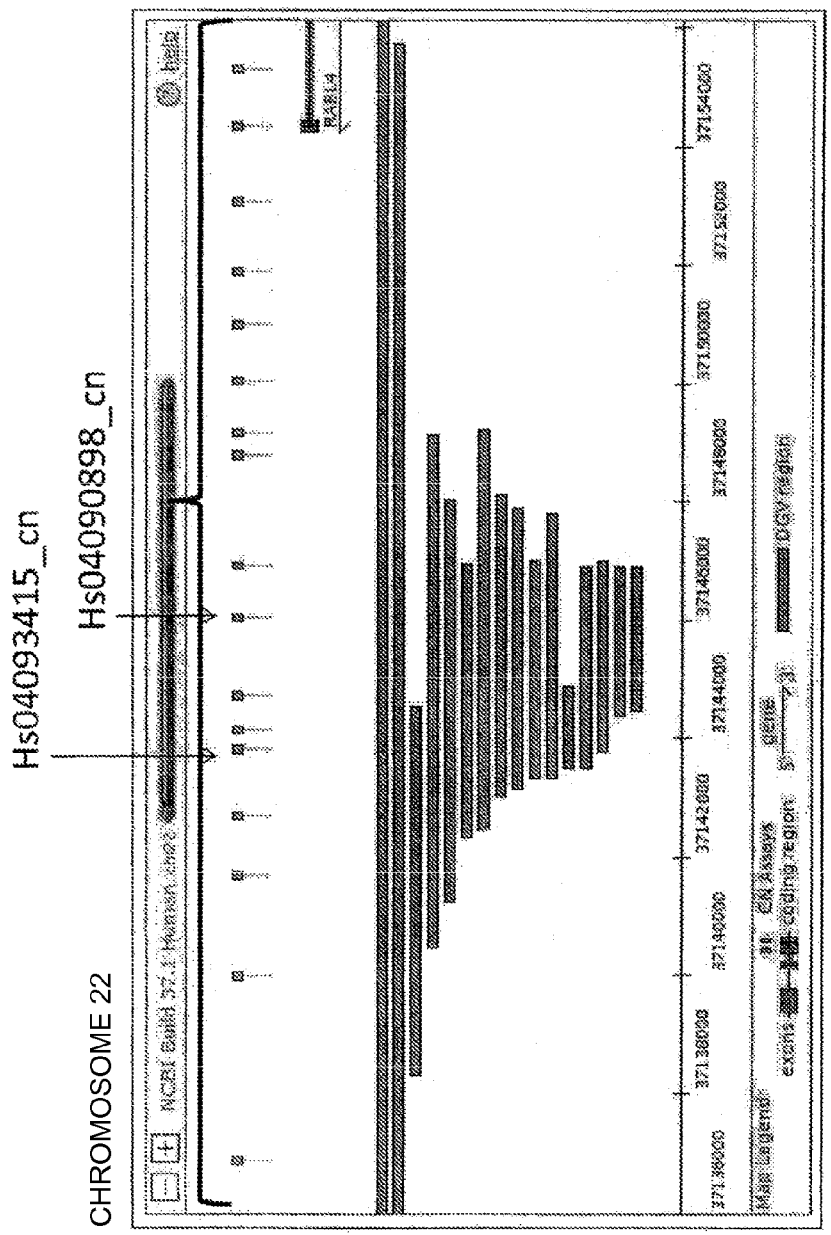
FIG. 4 is a diagram showing the chromosomal region of the DNA copy number polymorphism associated with breast cancer susceptibility detected by quantitative PCR with the primer set (Hs04093415_cn or Hs04090898_cn) in the chromosome 22q12.3 based on the human chromosome location information provided in "NCBI; February 2009 human reference sequence (Build 37.1)".

The method for determining breast cancer susceptibility according to the present invention is not particularly limited as long as it is a method for detecting at least one DNA copy number polymorphism in human chromosomal regions listed in the aforementioned [Group A] and a method for detecting a decrease of at least one DNA copy number in human chromosomal regions listed in the aforementioned [Group B] and/or an increase of at least one DNA copy number in human chromosomal regions listed in the aforementioned [Group C] (with the proviso that the diagnostic act performed by a doctor is excluded). Also, the kit for determining breast cancer susceptibility according to the present invention is not particularly limited as long as it is a kit including a primer set or probe, or a labeled primer set or probe for the detection of at least one DNA copy number polymorphism in human chromosomal regions listed in the aforementioned [Group A] and a kit including a primer set or probe, or a labeled primer set or probe for the detection of at least one DNA copy number polymorphism in human chromosomal regions listed in the aforementioned [Group B] and/or [Group C]. Here, the term "DNA copy number polymorphism" refers to a condition in which the genomic DNA copy number per cell is increased to more than two copies or decreased to less than two copies within a specific chromosomal region. Also, the term "detection of a DNA copy number polymorphism" refers to detecting the degree of increase or decrease in DNA copy number and the frequency of DNA copy number polymorphism. Here, "DNA copy number polymorphism" encompasses "gene copy number polymorphism."

The human chromosomal regions specified in the aforementioned [Group A], [Group B], and [Group C] are based on the human chromosomal location information provided in "NCBI; March 2006 human reference sequence (Build 36.1)". When there is a change in the human chromosomal location information by a version update and the like, the corresponding chromosomal region can be appropriately selected.

While breast cancer susceptibility can be determined by detecting a DNA copy number polymorphism in one region from among the human chromosomal regions listed in the aforementioned [Group A], DNA copy number polymorphism can also be detected in two or more regions, preferably three or more regions, and more preferably five or more regions to increase the precision of the determination. When DNA copy number polymorphisms are detected in a plurality of regions as described above, the microarray assay is preferably used as it enables detection with high throughput. Also, in order to more accurately detect an increase or decrease in copy number in a DNA copy number polymorphism, it is preferable that a human chromosomal regions listed in [Group B] and [Group C], which is a specific region selected from among the human chromosomal regions listed in [Group A] or located close to the human chromosomal regions listed in [Group A], are subjected to determination. Preferably, for example, the distance between the human chromosomal regions listed in [Group A] and regions close to them is preferably equal to or less than 10 kb (kilobases long), more preferably equal to or less than 5 kb, and particularly preferably equal to or less than 2 kb.

Examples of the aforementioned method for detecting a DNA copy number polymorphism include a detection method using, for example, microarray assay, quantitative polymerase chain reaction (PCR), loop-mediated isothermal amplification (LAMP), fluorescence in situ hybridization (FISH), smart amplification process (SMAP), etc. using human blood or human tissues as a detection sample. When detection is performed with high throughput, microarray assay is preferable, while when an increase or decrease in DNA copy number polymorphism is detected with high precision, quantitative PCR is preferable.

The microarray (microchip) used in the aforementioned microarray assay is a microarray (microchip) in which probes consisting of human chromosome fragments are fixed in a predetermined area on a support. The support of a microarray (microchip) may be any one that can be used for hybridization, and for example, a substrate such as glass, silicone, and plastic, a nitrocellulose membrane, and a nylon membrane are preferably used. While the microarray (microchip) can be produced by any method publicly known to those skilled in the art, a commercially available product can also be used. Examples of the commercially available product include 2.1M Array® manufactured by Roche, MAC Array® manufactured by Macrogen, Inc., SpectralChip® manufactured by Spectral Genomics, Inc., etc. Among them, 2.1M Array® manufactured by Roche can be given as a preferable example.

The aforementioned hybridization may be carried out, for example, to allow chromosomal DNA that is labeled with a fluorescent substance such as Cy-3 and Cy-5 in advance to hybridize to probes fixed to the surface of the microarray (microchip). The hybridization conditions may be appropriately selected from Molecular cloning, A laboratory manual, second edition, pp. 9.52 to 9.55 (1989), and the like.

Examples of the aforementioned quantitative PCR include competitive PCR, real-time PCR, etc. of which real-time PCR is preferable due to its high versatility. Examples of a method for detecting DNA amplified in real-time PCR include the TaqMan method using a fluorescent dye-conjugated probe (TaqMan probe) (Japanese Patent No. 2825976) and the intercalater method using an intercalater such as SYBR® Green I. Among them, the TaqMan method is preferable since it achieves higher specificity due to the specificity of primers combined with the specificity of probes. Real-time PCR can be performed using a specialized device for real-time PCR in which a common thermal cycler and a common spectrophotofluorometer are integrated.

In the method for determining breast cancer susceptibility according to the present invention, as long as the primer set used for the detection of the DNA copy number by quantitative PCR is capable of amplifying the chromosomal region to be detected, the length of the primer sequence, the annealing site in the human chromosomal region, and the like can be appropriately selected in consideration of DNA amplification efficiency and specificity. For the detection of the chromosomal regions listed in the aforementioned [Group B] and [Group C], for example, a primer set manufactured by Applied Biosystems can be obtained by searching a product number in the website of Applied Biosystems (www5.appliedbiosystems.com/tools/cnv/) and the like and ordering it. As specific examples, "1p36.12 (21,375,430 to 21,375,511) (SEQ ID NO: 1)" can be detected by the primer set "Hs06535529_cn", "3q26.1 (163,706,172 to 163,706,287) (SEQ ID NO: 2)" can be detected by the primer set "Hs03103056_cn", "15q26.3 (99,845,920 to 99,846,025) (SEQ ID NO: 3)" can be detected by the primer set "Hs03899300_cn", "15q26.3 (99,847,947 to 99,848,043) (SEQ ID NO: 4)" can be detected by the primer set "Hs03908783_cn", "15q26.3 (99,848,547 to 99,848,623) (SEQ ID NO: 5)" can be detected by the primer set "Hs03898338_cn", "22q12.3 (35,473,730 to 35,473,804) (SEQ ID NO: 6)" can be detected by the primer set "Hs04093415_cn", and "22q12.3 (35,475,937 to 35,476,043) (SEQ ID NO: 7)" can be detected by the primer set "Hs04090898_cn."

Examples of the aforementioned LAMP can include a method involving mixing materials such as a plurality of primers for amplifying a specific gene region, template DNA, strand-displacing DNA polymerase, and dNTP, allowing reactions to proceed at a certain temperature (around 65° C.) for a certain period of time, and then detecting the amplification based on the turbidity of the reaction solution.

Examples of the aforementioned FISH can include a technique involving performing hybridization between probe DNA, which has a DNA sequence capable of hybridizing to the target genomic region in a chromosome preparation and is labeled with a fluorescent substance such as fluorescein isothiocyanate (FITC), tetramethyl rhodamin isothiocyanate (TRITC), CyDye (R), and a chromosomal region, and counting the quantity of fluorescent signal resulting from the hybridization under a fluorescent microscope. Also, for DNA present on the same chromosome as the target region, an aberration in copy number can be more accurately evaluated by simultaneously performing hybridization using probes labeled with different kinds of fluorescence.

Examples of the aforementioned SMAP include a method involving mixing materials such as a plurality of primers for amplifying a specific gene region, template DNA, strand-displacing DNA polymerase, and dNTP, allowing reactions to proceed at a certain temperature (around 60° C.) for a certain period of time, and then detecting the amplification based on the fluorescent intensity of the reaction solution.

In order to increase the precision of the method for determining breast cancer susceptibility, it is preferable to perform a discriminant analysis by selecting two or more regions from the aforementioned [Group B] and/or [Group C]. In consideration of cost-effectiveness and workability, it is preferable to perform a discriminant analysis by selecting two regions. Examples of a combination of two regions to be selected include a combination of 1p36.12 (21,375,430 to 21,375,511)

consisting of the nucleotide sequence shown in SEQ ID NO: and 3q26.1 (163,706,172 to 163,706,287) consisting of the nucleotide sequence shown in SEQ ID NO: 2, a combination of 1p36.12 (21,375,430 to 21,375,511) consisting of the nucleotide sequence shown in SEQ ID NO: 1 and 22q12.3 (35,473,730 to 35,473,804) consisting of the nucleotide sequence shown in SEQ ID NO: 6, a combination of 1p36.12 (21,375,430 to 21,375,511) consisting of the nucleotide sequence shown in SEQ ID NO: 1 and 22q12.3 (35,475,937 to 35,476,043) consisting of the nucleotide sequence shown in SEQ ID NO: 7, a combination of 15q26.3 (99,845,920 to 99,846,025) consisting of the nucleotide sequence shown in SEQ ID NO: 3 and 3q26.1 (163,706,172 to 163,706,287) consisting of the nucleotide sequence shown in SEQ ID NO: 2, a combination of 15q26.3 (99,845,920 to 99,846,025) consisting of the nucleotide sequence shown in SEQ ID NO: 3 and 22q12.3 (35,473,730 to 35,473,804) consisting of the nucleotide sequence shown in SEQ ID NO: 6, a combination of 15q26.3 (99,845,920 to 99,846,025) consisting of the nucleotide sequence shown in SEQ ID NO: 3 and 22q12.3 (35,475,937 to 35,476,043) consisting of the nucleotide sequence shown in SEQ ID NO: 7, a combination of 15q26.3 (99,847,947 to 99,848,043) consisting of the nucleotide sequence shown in SEQ ID NO: 4 and 3q26.1 (163,706,172 to 163,706,287) consisting of the nucleotide sequence shown in SEQ ID NO: 2, a combination of 15q26.3 (99,847,947 to 99,848,043) consisting of the nucleotide sequence shown in SEQ ID NO: 4 and 22q12.3 (35,473,730 to 35,473,804) consisting of the nucleotide sequence shown in SEQ ID NO: 6, a combination of 15q26.3 (99,847,947 to 99,848,043) consisting of the nucleotide sequence shown in SEQ ID NO: 4 and 22q12.3 (35,475,937 to 35,476,043) consisting of the nucleotide sequence shown in SEQ ID NO: 7, a combination of 15q26.3 (99,848,547 to 99,848,623) consisting of the nucleotide sequence shown in SEQ ID NO: 5 and 3q26.1 (163,706,172 to 163,706,287) consisting of the nucleotide sequence shown in SEQ ID NO: 2, a combination of 15q26.3 (99,848,547 to 99,848,623) consisting of the nucleotide sequence shown in SEQ ID NO: 5 and 22q12.3 (35,473,730 to 35,473,804) consisting of the nucleotide sequence shown in SEQ ID NO: 6, a combination of 15q26.3 (99,848,547 to 99,848,623) consisting of the nucleotide sequence shown in SEQ ID NO: 5 and 22q12.3 (35,475,937 to 35,476,043) consisting of the nucleotide sequence shown in SEQ ID NO: 7, a combination of 1p36.12 (21,375,430 to 21,375,511) consisting of the nucleotide sequence shown in SEQ ID NO: 1 and 15q26.3 (99,845,920 to 99,846,025) consisting of the nucleotide sequence shown in SEQ ID NO: 3, a combination of 1p36.12 (21,375,430 to 21,375,511) consisting of the nucleotide sequence shown in SEQ ID NO: 1 and 15q26.3 (99,847,947 to 99,848,043) consisting of the nucleotide sequence shown in SEQ ID NO: 4, a combination of 1p36.12 (21,375,430 to 21,375,511) consisting of the nucleotide sequence shown in SEQ ID NO: 1 and 15q26.3 (99,848,547 to 99,848,623) consisting of the nucleotide sequence shown in SEQ ID NO: 5, a combination of 15q26.3 (99,845,920 to 99,846,025) consisting of the nucleotide sequence shown in SEQ ID NO: 3 and 15q26.3 (99,847,947 to 99,848,043) consisting of the nucleotide sequence shown in SEQ ID NO: 4, a combination of 15q26.3 (99,845,920 to 99,846,025) consisting of the nucleotide sequence shown in SEQ ID NO: 3 and 15q26.3 (99,848,547 to 99,848,623) consisting of the nucleotide sequence shown in SEQ ID NO: 5, a combination of 15q26.3 (99,847,947 to 99,848,043) consisting of the nucleotide sequence shown in SEQ ID NO: 4 and 15q26.3 (99,848,547 to 99,848,623) consisting of the nucleotide sequence shown in SEQ ID NO: 5, a combination of 3q26.1 (163,706,172 to 163,706,287) consisting of the nucleotide sequence shown in SEQ ID NO: 2 and 22q12.3 (35,473,730 to 35,473,804) consisting of the nucleotide sequence shown in SEQ ID NO: 6, a combination of 3q26.1 (163,706,172 to 163,706,287) consisting of the nucleotide sequence shown in SEQ ID NO: 2 and 22q12.3 (35,475,937 to 35,476,043) consisting of the nucleotide sequence shown in SEQ ID NO: 7, and a combination of 22q12.3 (35,473,730 to 35,473,804) consisting of the nucleotide sequence shown in SEQ ID NO: 6 and 22q12.3 (35,475,937 to 35,476,043) consisting of the nucleotide sequence shown in SEQ ID NO: 7. Among them, a combination of 15q26.3 (99,845,920 to 99,846,025) consisting of the nucleotide sequence shown in SEQ ID NO: 3 and 15q26.3 [99,847,947 to 99,848,043] consisting of the nucleotide sequence shown in SEQ ID NO: 4 is preferable.

The aforementioned discriminant analysis is not limited as long as it is a technique for obtaining a function (discriminant function) to determine as to, based on the data showing which sample (detection sample) belongs to which group (a group of healthy individuals or a group of breast cancer patients) prepared in advance, to which group a sample belongs, when the group to which the sample belongs is unknown. Among the discriminant functions, examples of a linear discriminant function include a hyperplane/linear discriminant function, etc. and examples of a non-linear discriminant function include a hypersurface/curved discriminant function based on the generalized Mahalanobis distance, etc.

In either of the following cases, an subject to be determined can be determined as highly susceptible to breast cancer (having a high risk of developing breast cancer): A significant increase in the DNA copy number is noted in an subject to be determined when a DNA copy number polymorphism is detected in each of the subject to be determined and a healthy individual (control) in at least one human chromosomal region selected from among the human chromosomal regions listed in the following [Group A-1], which is included in the aforementioned [Group A], and the resulting DNA copy numbers are compared between these individuals; or a significant decrease in the DNA copy number is noted in an subject to be determined when a DNA copy number polymorphism is detected in each of the subject to be determined and a healthy individual (control) in at least one human chromosomal region selected from among the human chromosomal regions listed in the following [Group A-2], which is included in the aforementioned [Group A], and the resulting DNA copy numbers are compared between these individuals.

[Group A-1]
1q44 (246,855,947-246,857,101)
1q44 (246,857,101-246,858,266)
22q12.3 (35,474,202-35,477,701)
[Group A-2]
2p16.3 (52,603,488-52,605,502)
2p16.3 (52,605,502-52,606,645)
2p16.3 (52,606,645-52,625,528)
2p16.3 (52,625,528-52,634,972)
2p16.3 (52,636,079-52,636,901)
3q26.1 (163,698,399-163,714,957)
3q26.1 (163,714,957-163,716,880)
3q26.1 (163,716,880-163,718,292)
6p25.3 (256,364-307,220)
6p25.3 (307,220-324,877)
7p13 (43,968,813-43,969,989)
7p13 (43,969,989-43,973,917)
7p13 (44,033,292-44,046,944)
7p13 (44,965,401-44,966,288)
8p11.23-p11.22 (39,351,598-39,352,968)
8p11.23-p11.22 (39,352,968-39,505,316)

8p11.23-p11.22 (39,505,316-39,506,703)
15q25.2 (80,700,012-80,703,055)
15q25.2 (80,703,055-80,704,239)
16p13.3 (1,374,245-1,386,928)
16p13.3 (1,409,635-1,451,145)
16p13.3 (2,530,856-2,531,917)
16p13.3 (4,688,278-4,689,410)
17p11.2 (18,864,114-18,866,684)
17q12 (33,593,624-33,606,100)
22q11.21 (18,698,449-18,701,734)
22q11.21 (18,708,863-18,718,104)
22q11.21 (18,744,485-18,751,648)
22q11.21 (18,751,648-18,757,015)
22q11.21 (18,763,247-18,764,375)
22q11.21 (18,764,375-18,766,608)
22q11.21 (18,766,608-18,767,909)
22q11.21 (18,767,909-18,803,304)
22q11.21 (18,851,650-18,854,853)
22q11.21 (18,861,035-18,862,757)
22q11.21 (20,129,733-20,132,553)
22q11.21 (20,139,367-20,140,478)
22q11.21 (20,142,316-20,143,929)
22q11.21 (20,157,427-20,158,507)
22q11.21 (20,158,507-20,163,759)
22q11.21 (20,163,759-20,166,938)
22q11.21 (20,166,938-20,189,915)
22q11.21 (20,189,915-20,194,583)
22q11.21 (20,194,583-20,198,780)
22q11.21 (20,198,780-20,206,030)
22q11.21 (20,206,030-20,233,462)
22q11.21 (20,233,462-20,239,367)
22q11.21 (20,239,367-20,243,220)
22q11.21 (20,243,220-20,244,301)
Xq26.3 (134,686,768-134,710,721)
Xq26.3 (134,715,826-134,718,277)

Further, in either of the following cases, an subject to be determined can be determined as less susceptible to breast cancer (having a low risk of developing breast cancer): A significant increase in the DNA copy number is noted in an subject to be determined when a DNA copy number polymorphism is detected in each of the subject to be determined and a healthy individual (control) in at least one human chromosomal region selected from among the human chromosomal regions listed in the following [Group A-3], which is included in the aforementioned [Group A], and the resulting DNA copy numbers are compared between these individuals; or a significant decrease in the DNA copy number is noted in an subject to be determined when a DNA copy number polymorphism is detected in each of the subject to be determined and a healthy individual (control) in at least one human chromosomal region selected from among the human chromosomal regions listed in the following [Group A-4], which is included in the aforementioned [Group A], and the resulting DNA copy numbers are compared between these individuals.

[Group A-3]
2p16.3 (52,603,488-52,605,502)
2p16.3 (52,605,502-52,606,645)
2p16.3 (52,606,645-52,611,965)
2p16.3 (52,611,965-52,620,153)
2p16.3 (52,620,153-52,622,543)
2p16.3 (52,622,543-52,636,901)
2p16.3 (52,636,901-52,638,223)
2q24.3 (165,544,576-165,563,420)
3q26.1 (163,701,862-163,705,223)
7q31.1 (109,240,145-109,241,260)
9p11.2 (43,752,248-43,754,446)
9q12-q13 (69,950,626-70,000,416)
9q12-q13 (70,000,416-70,026,246)
15q11.2 (19,054,967-19,055,863)
15q11.2 (20,081,406-20,091,581)
15q11.2 (20,091,581-20,146,200)
22q11.1 (14,529,177-14,551,306)
[Group A-4]
1p36.12 (21,373,559-21,374,437)
1p36.12 (21,374,437-21,376,929)
1p36.12 (21,376,929-21,378,068)
8p23.1 (7,331,151-7,366,894)
8p23.1 (7,384,482-7,385,717)
8p23.1 (7,385,717-7,675,644)
8p23.1 (7,675,644-7,677,003)
8p23.1 (7,729,310-7,756,222)
8p23.1 (7,766,308-7,785,964)
8p23.1 (7,789,316-7,796,881)
8p23.1 (7,796,881-7,804,843)
8p23.1 (7,804,843-7,812,725)
10p12.31 (22,644,992-22,646,132)
10p12.31 (22,646,132-22,647,050)
10p12.31 (22,648,356-22,654,917)
10p12.31 (22,654,917-22,656,057)
10q21.3 (66,977,059-66,982,379)
11q13.1 (64,298,883-64,299,791)
11q13.1 (64,299,791-64,300,705)
11q13.1 (64,300,705-64,303,775)
11q13.1 (64,303,775-64,305,075)
11q13.1 (64,305,075-64,309,752)
11q13.1 (64,309,752-64,310,507)
15q26.3 (99,847,229-99,848,361)
15q26.3 (99,848,361-99,851,910)
16p12.1 (22,587,790-22,590,317)
16p12.1 (22,602,200-22,605,904)
16p12.1 (22,605,904-22,610,525)
16p12.1 (22,612,746-22,614,711)
17q21.31 (39,786,143-39,789,781)
17q21.31 (39,789,781-39,791,475)
19q13.33 (55,769,626-55,774,306)
19q13.42 (60,579,276-60,581,130)
19q13.42 (60,581,130-60,582,666)
19q13.42 (60,582,666-60,588,237)
19q13.42 (60,588,237-60,589,160)
19q13.42 (60,589,160-60,589,969)
19q13.42 (60,597,122-60,598,638)
19q13.42 (60,598,638-60,599,772)
19q13.42 (60,599,772-60,601,009)
22q12.3 (35,472,904-35,474,202)

Further, in either of the following cases, an subject to be determined can be determined as highly susceptible to breast cancer (having a high risk of developing breast cancer): A significant decrease in the DNA copy number is noted in an subject to be determined when a DNA copy number polymorphism is detected in each of the subject to be determined and a healthy individual (control) in at least one human chromosomal region selected from among the human chromosomal regions listed in the aforementioned [Group B], and the resulting DNA copy numbers are compared between these individuals; or a significant increase in the DNA copy number is noted in an subject to be determined when a DNA copy number polymorphism is detected in each of the subject to be determined and a healthy individual (control) in at least one human chromosomal region selected from among the human chromosomal regions listed in the aforementioned [Group C], and the resulting DNA copy numbers are compared between these individuals. Also, the method for collecting data for the determination of breast cancer susceptibility and the method for collecting data for the prediction of the prognosis of breast cancer treatment according to the present invention include the step of collecting the results of detection of a DNA copy number polymorphism in an subject to be determined and a healthy individual (control) as data.

With regard to a primer set in the kit for determining breast cancer susceptibility according to the present invention, as long as it is a complementary primer set capable of annealing to a part of the upstream and downstream sequences of the chromosomal regions listed in [Group A], the length of the primer sequence, the annealing site in the human chromosomal region, the length of DNA to be amplified, and the like can be appropriately selected in consideration of DNA amplification efficiency and specificity. With respect to the chromosomal region to which the aforementioned primer set anneals, it is preferable that a human chromosomal regions listed in [Group B] and [Group C], which is a specific region selected from among the human chromosomal regions listed in [Group A] or located close to the human chromosomal regions listed in [Group A], are subjected to determination.

The probe in the kit for determining breast cancer susceptibility according to the present invention may be a probe hybridizing to all or a part of the human chromosomal regions listed in [Group A]. With respect to the chromosomal region to which the aforementioned probe hybridizes, it is preferable that a human chromosomal regions listed in [Group B] and [Group C], which is a specific region selected from among the human chromosomal regions listed in [Group A] or the regions close to the human chromosomal regions listed in [Group A], are subjected to determination. Examples of the label attached to the aforementioned probe can include biotin, fluorescein, $^{32}$P, etc.

Hereinbelow, the present invention will be described further in detail with reference to Examples. However, the technical scope of the present invention is not limited to these Examples.

EXAMPLES

Example 1

1. Identification of a DNA Copy Number Polymorphic Region Associated with Breast Cancer Susceptibility by Microarray Assay
1-1 Materials
[1] DNA (30 samples) extracted from the peripheral blood of 30 healthy females (Group of healthy individuals)
[2] DNA (30 samples) extracted from the peripheral blood of 30 sporadic breast cancer patients (Group of breast cancer patients)
[3] DNA pool, which contains DNA extracted from the peripheral blood of 30 healthy females combined in one tube (Reference DNA)
1-2 Method
1-2-1 Fluorescent labeling of DNA (Nimblegen Dual-Color DNA Labeling Kit [Roche] was used according to the product protocol)
Cy3-Random Nonamer and Cy5-Random Nonamer are each diluted by adding 998.25 μl of a Random Primer Buffer and 1.75 μl of β mercaptoethanol in advance.
(1) Labeling of Test DNA
[1] Prepare two 0.5 ml tubes and place the following materials in each tube:
Test DNA (1 μg) (DNA derived from the peripheral blood of breast cancer patients or healthy females),
Diluted Cy-3-Random Nonamers (40 μl), and
Nuclease-free water (in an amount to bring the total volume to 80 μl).
[2] Incubate at 98° C. for 10 minutes, and then for two minutes on ice.
[3] Add the following reagents to each tube:
10 mM dNTP Mix (10 μl),
Nuclease-free water (8 μl), and
50 U/μl Klenow Fragment (2 μl).
[4] Incubate at 37° C. overnight.
[5] Add 10 μl of a stop solution (0.5 M EDTA) to each tube.
[6] Add 11.5 μl of 5M NaCl to each tube.
[7] Add 110 μl of isopropanol to each tube.
[8] Combine the contents of the two tubes in one 1.5 ml tube.
[9] After thoroughly mixing, incubate at room temperature for 10 minutes.
[10] After centrifuging at 12,000 g for 10 minutes, pipet out the supernatant.
[11] After adding 500 μl of cooled 80% ethanol to each tube, centrifuge at 12,000 g for two minutes, and pipet out the supernatant.
[12] Naturally dry DNA in a light-shielded environment to pelletize it.
[13] Store the resulting DNA at −20° C.
(2) Labeling of Reference DNA
[1] Prepare two 0.5 ml tubes and place the following materials in each tube:
Reference DNA (1 μg) (DNA pool derived from the peripheral blood of 30 healthy females),
Diluted Cy-5-Random Nonamers (40 μl), and
Nuclease-free water (in an amount to bring the total volume to 80 μl).
[2] Incubate at 98° C. for 10 minutes, and then for two minutes on ice.
[3] Add the following reagents to each tube:
10 mM dNTP Mix (10 μl),
Nuclease-free water (8 μl), and
50 U/μl Klenow Fragment (2 μl).
[4] Incubate at 37° C. overnight.
[5] Add 10 μl of a stop solution (0.5 M EDTA) to each tube.
[6] Add 11.5 μl of 5M NaCl to each tube.
[7] Add 110 μl of isopropanol to each tube.
[8] Combine the contents of the two tubes in one 1.5 ml tube.
[9] After thoroughly mixing, incubate at room temperature for 10 minutes.
[10] After centrifuging at 12,000 g for 10 minutes, pipet out the supernatant.
[11] After adding 500 μl of cooled 80% ethanol to each tube, centrifuge at 12,000 g for two minutes, and pipet out the supernatant.
[12] Naturally dry DNA in a light-shielded environment to pelletize it.
[13] Store the resulting DNA at −20° C.
1-2-2 Hybridization
[1] After adding 20 μl of purified water to each pellet, leave the pellet for 20 minutes, followed by vortexing.
[2] Measure the DNA concentration.
[3] Place the following materials into a 0.5 ml tube:
Fluorescently-labeled test DNA (34 μg),
Fluorescently-labeled reference DNA (34 μg), and
purified water (in an amount to bring the total volume to 12.3 μl).
[4] Place the following reagents included in the NimbleGen Hybridization Kit (manufactured by Roche) in a 0.5 ml tube:
2× Hybridization Buffer (29.5 μl),
Hybridization Component A (11.8 μl), and
Alignment Oligo (1.2 μl).
[5] Add 31.7 μl of the solution prepared in [4] into the solution prepared in [3].

[6] Incubate at 95° C. for five minutes, then at 42° C. for five minutes or longer.
[7] Set the Nimblegen HX1 Mixer (manufactured by Roche) in the 2.1M array (manufactured by Roche) and place the array on a heat block at 42° C.
[8] Pour 41 μl of the solution prepared in [5] into the 2.1M array.
[9] Set the 2.1M array slide in the Nimblegen hybridization system (manufactured by Roche) and carry out hybridization for 72 hours.

1-2-3 Washing (Using the NimbleGen Wash Buffer Kit and the NimbleGen Array Processing Accessories (Manufactured by Roche))
[1] Prepare Wash solutions 1, 2, and 3.
1) Wash Solution 1 (2 Sets)
Water (manufactured by VWR) (225 ml)
10× Wash Buffer I (25 ml)
1M DTT (25 μl)
2) Wash Solution 2 (1 Set)
Water (manufactured by VWR) (225 ml)
10× Wash Buffer II (25 ml)
1M DTT (25 μl)
3) Wash Solution 3 (1 Set)
Water (manufactured by VWR) (225 ml)
10× Wash Buffer III (25 ml)
1M DTT (25 μl)
[2] Immerse the 2.1M array in Wash solution 1 that has been warmed to 40° C. in advance to remove the Nimblegen HX1 Mixer.
[3] Shake the 2.1M array in Wash solution 1 for 10 to 15 seconds to wash out the hybridization buffer.
[4] Wash the 2.1M array in Wash solution 1 (room temperature) by thoroughly shaking for two minutes.
[5] Wash the 2.1M array in Wash solution 2 (room temperature) by thoroughly shaking for one minute.
[6] Wash the 2.1M array in Wash solution 3 (room temperature) by thoroughly shaking for 15 seconds.
[7] Dry the slide using a centrifuge.

1-2-4 Scanning of the Array Slide and Data Analysis
[1] Set the 2.1M array in the microarray scanner GenePix 4000 B (manufactured by Axon instruments) and scan the fluorescence of the array.
[2] Analyze the fluorescence image file thus obtained by the NimbleScan v2.5 software (manufactured by Roche) to obtain the fluorescence intensity information of each probe in the 2.1M array.
[3] Compare the copy number polymorphic regions between healthy individuals and breast cancer patients by the Nexus copy number software (version 5, manufactured by Bio-Discovery, Inc.) to identify the CNP region associated with the development of breast cancer.

Example 2

2. A Verification Test by Quantitative PCR
Based on the data obtained by the microarray assay, CNP in the regions 1p36.12, 3q26.1, 15q26.3, and 22q12.3 was evaluated by quantitative PCR. Also, as a control, the number of copies of the ribonuclease P (RNase P) (SEQ ID NO: 8) gene region on chromosome 14 was quantitated.

2-1 Materials
[1]: DNA (216 samples) extracted from the peripheral blood of healthy females (Group of healthy individuals)
[2]: DNA (193 samples) extracted from the peripheral blood of breast cancer patients (females) (Group of breast cancer patients)
[3]: DNA pool containing DNA extracted from the peripheral blood of 30 healthy females prepared in 1-1 [3] (Reference DNA)

2-2 Method
[1] Add the following reagents:
5 ng/μl DNA (2 μl),
TaqMan Genotyping Master Mix (manufactured by Applied Biopsystems) (5 μl),
TaqMan Copy Number Assay probe and primer set (manufactured by Applied Biopsystems) (0.5 μl),
TaqMan Copy Number Reference Assay RNase P (manufactured by Applied Biopsystems) (0.5 μl), and
Purified water (2 μl)

With respect to the PCR primers and probes, pre-designed products were searched in the website of Applied Biosystems (www5.appliedbiosystems.com/tools/cnv/) and used. The TaqMan Copy Number Assay probe and primer sets used are shown in the following table 1 and FIGS. 1 to 4 (see the website of Applied Biosystems www5.appliedbiosystems.com/tools/cnv/). Also, the nucleotide sequence of the chromosomal region amplified by quantitative PCR was identified by the method described in the following section "[3] Quantitative PCR analysis and identification of the nucleotide sequence of the PCR amplification product" (see "Nucleotide sequence of the PCR-amplified region" in Table 1). Based on the nucleotide sequence thus identified, the location information of the chromosomal regions amplified by quantitative PCR was shown based on NCBI; March 2006 human reference sequence (Build 36.1) (see "Chromosomal region" in Table 1).

TABLE 1

| Copy number Assay ® ID | Nucleotide sequence of the PCR-amplified region (5'-3') | Chromosomal region (NCBI36/hg18) |
| --- | --- | --- |
| Hs06535 529_cn | TCGCTGTGCCTGATTTCAGAGCCGGTTTCTGCGGTAAACTC ATGGCAAAGCGAAGCCACCAACCCCCCCAGAGCGGGACCGG (SEQ ID NO: 1) | 1p36. 12: 21,375,430- 21,375,511 |
| Hs03103 056_cn | TGGCAACATCTCAATATCCRCAGAATTTTCATATTTATCCA GGTAGAATTGATAAACAGAAAATTCCACAAGAACCATAAAT TATTTAACACATACACACACACACTCAAATTTAG (SEQ ID NO: 2) | 3q26. 1: 163,706,172- 163,706,287 |
| Hs03899 300_cn | ACTGCCTGGCACTAAGGTTTAGAGTTATGAGTCGGTGCTTC CCTGTCACTTCACTTAACCCTCTGAGTGTGCAGTTTGTAGA TTTGTTAACTGCACTGAGAGGTCC (SEQ ID NO: 3) | 15q26. 3: 99,845,920- 99,846,025 |

TABLE 1-continued

| Copy number Assay ® ID | Nucleotide sequence of the PCR-amplified region (5'-3') | Chromosomal region (NCBI36/hg18) |
|---|---|---|
| Hs03908 783_cn | GCCTGCCTCCCRGCATGGGCCGCGGCCTCCGCCATGGGCTC CGTGCGGTGGTTTCTCGGGTACACGCTCGTGAGCCYGGCTG ATGCGCCACATGCCT (SEQ ID NO: 4) | 15q26. 3: 99,847,947- 99,848,043 |
| Hs03898 338_cn | ATCGCTGCTGGATCTCTTCTGTCATCCCTCCCAGGACCCAT TGGTCCTACTGGCCCACTTCCAGAAAGCAAGCCATC (SEQ ID NO: 5) | 15q26. 3: 99,848,547- 99,848,623 |
| Hs04093 415_cn | GTGTCGAGGCTGCTCCTTAAAYGCTTCTTGCCTGCACGCTG TGCGTGGAAACCCAAAGAAGTGAGAGACGCGAGG (SEQ ID NO: 6) | 22q12. 3: 35,473,730- 35,473,804 |
| Hs04090 898_cn | CTCCTAGTGGGATCCTACAACTCTCAGAACAACAGGGTCCC CCTGGACTGTGAGCACAGTAGAACCAGCTCTTTCTTGGGAT TTAAGAAAACAGACAAGCTTCGCG (SEQ ID NO: 7) | 22q12. 3: 35,475,937- 35,476,043 |
| RNaseP (Reference) | CCCTAGTCTCAGACCTTCCCAAGGGACATGGGAGTGGAGTG ACAGRACGCACTCAGCTCGTGGCCCCACTGATGAGCTTCCC TCCGC (SEQ ID NO: 8) | 14q11. 2: 19,881,319- 19,881,405 |

[2] Quantitative PCR

Using the 7900HT Fast Real-Time PCR System (manufactured by Applied Biopsystems), PCR reactions were carried out as shown in the following Table 2.

TABLE 2

| Stage | Temperature | Time |
|---|---|---|
| Hold | 95° C. | 10 Minutes |
| Cycle (40 Cycles) | 95° C. | 15 Seconds |
|  | 60° C. | 60 Seconds |

[3] Quantitative PCR Analysis and Identification of the Nucleotide Sequence of the PCR Amplification Product Using the CopyCaller software (manufactured by Applied Biopsystems), the number of copies of the TaqMan Copy Number Assay probe and primer set was analyzed. Assuming that the number of copies of the TaqMan Copy Number Assay probe and primer set with respect to Reference DNA (RNaseP, SEQ ID NO: 8) is 2, a relative copy number was calculated for the test samples. In order to identify the nucleotide sequence of the PCR product amplified by quantitative PCR, the PCR product was cloned into the pGEM (R)-T Easy vector (manufactured by Promega K.K.) and a nucleotide sequence-detection sample was prepared using the BigDye Terminator Cycle Sequencing Kit (manufactured by Applied Biosystems). Then, the PCR product was sequenced by a DNA sequencer (manufactured by Applied Biosystems).

Example 3

3. Results 3-1 Results of the Microarray Assay

In comparing the group of breast cancer patients with the group of healthy individuals, the CNP regions in which [1] the copy number alteration occurred at a frequency of 25% or more in either group, and [2] there was a statistically significant difference in the frequency of copy number alteration (P<0.05 by the Fisher's test) between the above two groups are shown in the following Tables 3 to 6.

TABLE 3

| Chromosomal locus (NCBI Build 36) | Region (NCBI build 36) | Length of region (bases) | Copy number alteration | Frequency in the group of healthy females (%) | Frequency in the group of breast cancer patients (%) | P Value | Odds ratio |
|---|---|---|---|---|---|---|---|
| 1q44 | 246,855,947-246,857,101 | 1,154 | Increase | 26.7 | 56.7 | 0.035 | 3.60 |
|  | 246,857,101-246,858,266 | 1,165 |  | 23.3 | 53.3 | 0.033 | 3.76 |
| 1p36. 12 | 21,373,559-21,374,437 | 878 | Decrease | 36.7 | 3.3 | 0.002 | 0.06 |
|  | 21,374,437-21,376,929 | 2,492 |  | 40.0 | 3.3 | 0.001 | 0.05 |
|  | 21,376,929-21,378,068 | 1,139 |  | 36.7 | 6.7 | 0.010 | 0.12 |
| 2p16. 3 | 52,603,488-52,605,502 | 2,014 | Increase | 83.3 | 53.3 | 0.025 | 0.23 |
|  | 52,605,502-52,606,645 | 1,143 |  | 83.3 | 56.7 | 0.047 | 0.26 |
|  | 52,606,645-52,611,965 | 5,320 |  | 90.0 | 56.7 | 0.007 | 0.15 |
|  | 52,611,965-52,620,153 | 8,188 |  | 93.3 | 56.7 | 0.002 | 0.09 |
|  | 52,620,153-52,622,543 | 2,390 |  | 90.0 | 56.7 | 0.007 | 0.15 |
|  | 52,622,543-52,636,901 | 14,358 |  | 86.7 | 56.7 | 0.020 | 0.20 |
|  | 52,636,901-52,638,223 | 1,322 |  | 83.3 | 53.3 | 0.025 | 0.23 |
| 2q24. 3 | 165,544,576-165,563,420 | 18,844 | Increase | 26.7 | 0.0 | 0.005 | 0.04 |
| 2p16. 3 | 52,603,488-52,605,502 | 2,014 | Decrease | 0.0 | 30.0 | 0.002 | 26.95 |
|  | 52,605,502-52,606,645 | 1,143 |  | 3.3 | 33.3 | 0.006 | 14.50 |
|  | 52,606,645-52,625,528 | 18,883 |  | 6.7 | 40.0 | 0.005 | 9.33 |
|  | 52,625,528-52,634,972 | 9,444 |  | 6.7 | 35.7 | 0.010 | 8.11 |
|  | 52,636,079-52,636,901 | 822 |  | 3.3 | 30.0 | 0.012 | 12.43 |

TABLE 3-continued

| Chromosomal locus (NCBI Build 36) | Region (NCBI build 36) | Length of region (bases) | Copy number alteration | Frequency in the group of healthy females (%) | Frequency in the group of breast cancer patients (%) | P Value | Odds ratio |
|---|---|---|---|---|---|---|---|
| 3q26.1 | 163,701,862-163,705,223 | 3,361 | Increase | 56.7 | 26.7 | 0.035 | 0.28 |
| 3q26.1 | 163,698,399-163,714,957 | 16,558 | Decrease | 10.0 | 43.3 | 0.007 | 6.88 |
| | 163,714,957-163,716,880 | 1,923 | | 10.0 | 40.0 | 0.015 | 6.00 |
| | 163,716,880-163,718,292 | 1,412 | | 6.7 | 33.3 | 0.021 | 7.00 |
| 6p25.3 | 256,364-307,220 | 50,856 | Decrease | 13.3 | 43.3 | 0.020 | 4.97 |
| | 307,220-324,877 | 17,657 | | 16.7 | 43.3 | 0.047 | 3.82 |
| 7q31.1 | 109,240,145-109,241,260 | 1,115 | Increase | 36.7 | 10.0 | 0.030 | 0.19 |
| 7p13 | 43,968,813-43,969,989 | 1,176 | Decrease | 16.7 | 46.7 | 0.025 | 4.38 |
| | 43,969,989-43,973,917 | 3,928 | | 16.7 | 50.0 | 0.013 | 5.00 |
| | 44,033,292-44,046,944 | 13,652 | | 26.7 | 56.7 | 0.035 | 3.60 |
| 7p13 | 44,965,401-44,966,288 | 887 | Decrease | 0.0 | 26.7 | 0.005 | 23.04 |

TABLE 4

| Chromosomal locus (NCBI Build 36) | Region (NCBI build 36) | Length of region (bases) | Copy number alteration | Frequency in the group of healthy females (%) | Frequency in the group of breast cancer patients (%) | P Value | Odds ratio |
|---|---|---|---|---|---|---|---|
| 8p23.1 | 7,331,151-7,366,894 | 35,743 | Decrease | 40.0 | 13.3 | 0.039 | 0.23 |
| | 7,384,482-7,385,717 | 1,235 | | 43.3 | 13.3 | 0.020 | 0.20 |
| | 7,385,717-7,675,644 | 289,927 | | 43.3 | 16.7 | 0.047 | 0.26 |
| | 7,675,644-7,677,003 | 1,359 | | 43.3 | 13.3 | 0.020 | 0.20 |
| | 7,729,310-7,756,222 | 26,912 | | 40.0 | 13.3 | 0.039 | 0.23 |
| | 7,766,308-7,785,964 | 19,656 | | 40.0 | 13.3 | 0.039 | 0.23 |
| | 7,789,316-7,796,881 | 7,565 | | 43.3 | 16.7 | 0.047 | 0.26 |
| | 7,796,881-7,804,843 | 7,962 | | 43.3 | 13.3 | 0.020 | 0.20 |
| | 7,804,843-7,812,725 | 7,882 | | 40.0 | 13.3 | 0.039 | 0.23 |
| 8p11.23-p11.22 | 39,351,598-39,352,968 | 1,370 | Decrease | 13.3 | 40.0 | 0.039 | 4.33 |
| | 39,352,968-39,505,316 | 152,348 | | 13.3 | 43.3 | 0.020 | 4.97 |
| | 39,505,316-39,506,703 | 1,387 | | 13.3 | 40.0 | 0.039 | 4.33 |
| 9p11.2 | 43,752,248-43,754,446 | 2,198 | Increase | 30.0 | 3.3 | 0.012 | 0.08 |
| 9q12-q13 | 69,950,626-70,000,416 | 49,790 | Increase | 40.0 | 13.3 | 0.039 | 0.23 |
| | 70,000,416-70,026,246 | 25,830 | | 36.7 | 10.0 | 0.030 | 0.19 |
| 10p12.31 | 22,644,992-22,646,132 | 1,140 | Decrease | 26.7 | 0.0 | 0.005 | 0.04 |
| | 22,646,132-22,647,050 | 918 | | 30.0 | 0.0 | 0.002 | 0.04 |
| | 22,648,356-22,654,917 | 6,561 | | 40.0 | 10.0 | 0.015 | 0.17 |
| | 22,654,917-22,656,057 | 1,140 | | 36.7 | 10.0 | 0.030 | 0.19 |
| 10q21.3 | 66,977,059-66,982,379 | 5,320 | Decrease | 30.0 | 3.3 | 0.012 | 0.08 |
| 11q13.1 | 64,298,883-64,299,791 | 908 | Decrease | 40.0 | 13.3 | 0.039 | 0.23 |
| | 64,299,791-64,300,705 | 914 | | 40.0 | 10.0 | 0.015 | 0.17 |
| | 64,300,705-64,303,775 | 3,070 | | 40.0 | 10.0 | 0.015 | 0.17 |
| | 64,303,775-64,305,075 | 1,300 | | 40.0 | 10.0 | 0.015 | 0.17 |
| | 64,305,075-64,309,752 | 4,677 | | 40.0 | 10.0 | 0.015 | 0.17 |
| | 64,309,752-64,310,507 | 755 | | 33.3 | 6.7 | 0.021 | 0.17 |

TABLE 5

| Chromosomal locus (NCBI Build 36) | Region (NCBI build 36) | Length of region (bases) | Copy number alteration | Frequency in the group of healthy females (%) | Frequency in the group of breast cancer patients (%) | P Value | Odds ratio |
|---|---|---|---|---|---|---|---|
| 15q11.2 | 19,054,967-19,055,863 | 896 | Increase | 36.7 | 10.0 | 0.030 | 0.19 |
| 15q11.2 | 20,081,406-20,091,581 | 10,175 | Increase | 36.7 | 10.0 | 0.030 | 0.19 |
| | 20,091,581-20,146,200 | 54,619 | | 36.7 | 6.7 | 0.010 | 0.12 |
| 15q25.2 | 80,700,012-80,703,055 | 3,043 | Decrease | 20.0 | 53.3 | 0.015 | 4.57 |
| | 80,703,055-80,704,239 | 1,184 | | 23.3 | 53.3 | 0.033 | 3.76 |
| 15q26.3 | 99,847,229-99,848,361 | 1,132 | Decrease | 36.7 | 6.7 | 0.010 | 0.12 |
| | 99,848,361-99,851,910 | 3,549 | | 36.7 | 10.0 | 0.030 | 0.19 |
| 16p13.3 | 1,374,245-1,386,928 | 12,683 | Decrease | 16.7 | 43.3 | 0.047 | 3.82 |
| | 1,409,635-1,451,145 | 41,510 | | 16.7 | 43.3 | 0.047 | 3.82 |
| 16p13.3 | 2,530,856-2,531,917 | 1,061 | Decrease | 10.0 | 36.7 | 0.030 | 5.21 |
| 16p13.3 | 4,688,278-4,689,410 | 1,132 | Decrease | 13.3 | 40.0 | 0.039 | 4.33 |
| 16p12.1 | 22,587,790-22,590,317 | 2,527 | Decrease | 40.0 | 13.3 | 0.039 | 0.23 |
| | 22,602,200-22,605,904 | 3,704 | | 40.0 | 13.3 | 0.039 | 0.23 |
| | 22,605,904-22,610,525 | 4,621 | | 36.7 | 10.0 | 0.030 | 0.19 |
| | 22,612,746-22,614,711 | 1,965 | | 33.3 | 6.7 | 0.021 | 0.14 |

TABLE 5-continued

| Chromosomal locus (NCBI Build 36) | Region (NCBI build 36) | Length of region (bases) | Copy number alteration | Frequency in the group of healthy females (%) | Frequency in the group of breast cancer patients (%) | P Value | Odds ratio |
|---|---|---|---|---|---|---|---|
| 17p11.2 | 18,864,114-18,866,684 | 2,570 | Decrease | 16.7 | 43.3 | 0.047 | 3.82 |
| 17p12 | 33,593,624-33,606,100 | 12,476 | Decrease | 16.7 | 43.3 | 0.047 | 3.82 |
| 17q21.31 | 39,786,143-39,789,781 | 3,638 | Decrease | 33.3 | 3.3 | 0.006 | 0.07 |
|  | 39,789,781-39,791,475 | 1,694 |  | 30.0 | 3.3 | 0.012 | 0.08 |
| 19q13.33 | 55,769,626-55,774,306 | 4,680 | Decrease | 30.0 | 3.3 | 0.012 | 0.08 |
| 19q13.42 | 60,579,276-60,581,130 | 1,854 | Decrease | 43.3 | 16.7 | 0.047 | 0.26 |
|  | 60,581,130-60,582,666 | 1,536 |  | 53.3 | 23.3 | 0.033 | 0.27 |
|  | 60,582,666-60,588,237 | 5,571 |  | 56.7 | 20.0 | 0.007 | 0.19 |
|  | 60,588,237-60,589,160 | 923 |  | 53.3 | 20.0 | 0.015 | 0.22 |
|  | 60,589,160-60,589,969 | 809 |  | 40.0 | 13.3 | 0.039 | 0.23 |
| 19q13.42 | 60,597,122-60,598,638 | 1,516 | Decrease | 36.7 | 10.0 | 0.030 | 0.19 |
|  | 60,598,638-60,599,772 | 1,134 |  | 36.7 | 6.7 | 0.010 | 0.12 |
|  | 60,599,772-60,601,009 | 1,237 |  | 33.3 | 6.7 | 0.021 | 0.14 |

TABLE 6

| Chromosomal locus (NCBI Build 36) | Region (NCBI build 36) | Length of region (bases) | Copy number alteration | Frequency in the group of healthy females (%) | Frequency in the group of breast cancer patients (%) | P Value | Odds ratio |
|---|---|---|---|---|---|---|---|
| 22q11.1 | 14,529,177-14,551,306 | 22,129 | Increase | 26.7 | 0.0 | 0.005 | 0.04 |
| 22q12.3 | 35,474,202-35,477,701 | 3,499 | Increase | 13.3 | 40.0 | 0.039 | 4.33 |
| 22q11.21 | 18,698,449-18,701,734 | 3,285 | Decrease | 6.7 | 33.3 | 0.021 | 7.00 |
|  | 18,708,863-18,718,104 | 9,241 |  | 10.0 | 36.7 | 0.030 | 5.21 |
|  | 18,744,485-18,751,648 | 7,163 |  | 33.3 | 66.7 | 0.019 | 4.00 |
|  | 18,751,648-18,757,015 | 5,367 |  | 36.7 | 66.7 | 0.038 | 3.46 |
|  | 18,763,247-18,764,375 | 1,128 |  | 36.7 | 66.7 | 0.038 | 3.46 |
|  | 18,764,375-18,766,608 | 2,233 |  | 33.3 | 70.0 | 0.009 | 4.67 |
|  | 18,766,608-18,767,909 | 1,301 |  | 33.3 | 66.7 | 0.019 | 4.00 |
|  | 18,767,909-18,803,304 | 35,395 |  | 33.3 | 63.3 | 0.038 | 3.46 |
|  | 18,851,650-18,854,853 | 3,203 |  | 36.7 | 66.7 | 0.038 | 3.46 |
|  | 18,861,035-18,862,757 | 1,722 |  | 36.7 | 66.7 | 0.038 | 3.46 |
| 22q11.21 | 20,129,733-20,132,553 | 2,820 | Decrease | 6.7 | 33.3 | 0.021 | 7.00 |
|  | 20,139,367-20,140,478 | 1,111 |  | 13.3 | 40.0 | 0.039 | 4.33 |
|  | 20,142,316-20,143,929 | 1,613 |  | 23.3 | 53.3 | 0.033 | 3.76 |
|  | 20,157,427-20,158,507 | 1,080 |  | 26.7 | 56.7 | 0.035 | 3.60 |
|  | 20,158,507-20,163,759 | 5,252 |  | 26.7 | 56.7 | 0.035 | 3.60 |
|  | 20,163,759-20,166,938 | 3,179 |  | 26.7 | 56.7 | 0.035 | 3.60 |
|  | 20,166,938-20,189,915 | 22,977 |  | 26.7 | 60.0 | 0.018 | 4.13 |
|  | 20,189,915-20,194,583 | 4,668 |  | 23.3 | 60.0 | 0.008 | 4.93 |
|  | 20,194,583-20,198,780 | 4,197 |  | 23.3 | 60.0 | 0.008 | 4.93 |
|  | 20,198,780-20,206,030 | 7,250 |  | 23.3 | 60.0 | 0.008 | 4.93 |
|  | 20,206,030-20,233,462 | 27,432 |  | 26.7 | 60.0 | 0.018 | 4.13 |
|  | 20,233,462-20,239,367 | 5,905 |  | 23.3 | 56.7 | 0.017 | 4.30 |
|  | 20,239,367-20,243,220 | 3,853 |  | 20.0 | 53.3 | 0.015 | 4.57 |
|  | 20,243,220-20,244,301 | 1,081 |  | 20.0 | 50.0 | 0.029 | 4.00 |
| 22q12.3 | 35,472,904-35,474,202 | 1,298 | Decrease | 76.7 | 46.7 | 0.033 | 0.27 |
| Xq26.3 | 134,686,768-134,710,721 | 23,953 | Decrease | 13.3 | 40.0 | 0.039 | 4.33 |
|  | 134,715,826-134,718,277 | 2,451 |  | 10.0 | 36.7 | 0.030 | 5.21 |

The term "odds ratio" in the Tables is an index indicating the relevance between the cause (DNA copy number polymorphism) and result (breast cancer), and the odds ratio is distributed from 0 to infinity. When the odds ratio is less than 1, an individual having the DNA copy number polymorphism can be determined as less susceptible to breast cancer, whereas when the odds ratio is more than 1, an individual having the DNA copy number polymorphism can be determined as highly susceptible to breast cancer. Taking the top data in Table 3 as an example, the frequency of an increase in the number of copies of the regions 246,855,947 to 246,857,101 (1,154 bases long) in the chromosomal locus 1q44 was eight out of 30 individuals (26.7%) in the group of healthy individuals, whereas the frequency was 17 out of 30 individuals (56.7%) in the group of breast cancer patients, revealing a significantly high frequency of copy number increase in the above region (P=0.035, odds ratio 3.6) in the breast cancer patients. As demonstrated above, it was revealed that a region enabling prediction of a predisposition to breast cancer was present in each CNP.

3-2 Results of the Quantitative PCR (1) Quantitative PCR

Using the chromosomal regions shown in Tables 3 to 6 as identified by the microarray assay and regions close to them, quantitative PCR was performed according to the method described in the aforementioned section "2-2 Method". Specifically, a total of the following seven regions was used: "1p36.12 21,375,430 to 21,375,511", "3q26.1 163,706,172 to 163,706,287", "15q26.3 99,845,920 to 99,846,025", "15q26.3 99,847,947 to 99,848,043", "15q26.3 99,848,547 to 99,848,623", "22q12.3 35,473,730 to 35,473,804", and "22q12.3 35,475,937 to 35,476,043."

Figure 5:
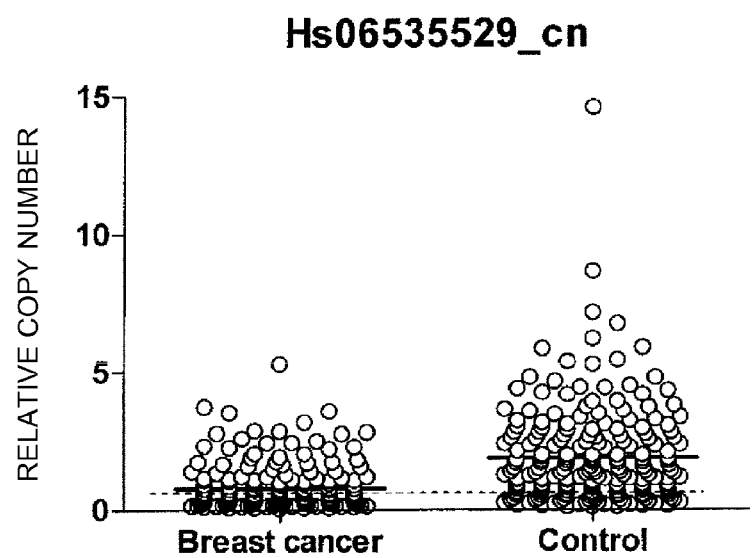
FIG. 5 is a diagram showing the results of the DNA copy number polymorphism detected by quantitative PCR with the primer set (Hs06535529_cn) in the group of healthy individuals (Control) and the group of breast cancer patients (Breast cancer). The horizontal line indicates the mean value in each group. The dotted line indicates the cut-off value. The symbol ○ indicates the number of copies in each individual.

[1] FIG. 5 and Table 7 (Hs06535529_cn): A DNA copy number of less than 0.5 in the chromosomal region (1p36.12

[21,375,430 to 21,375,511]), which is amplified by the primer set (Hs06535529_cn), was observed in 36 out of 216 individuals (16.7%) in the group of healthy individuals, whereas that was observed in 107 out of 193 individuals (55.4%) in the group of breast cancer patients, revealing a significantly high frequency of DNA copy number of less than 0.5 (P<0.0001, odds ratio of 6.2, Fisher's test) in the group of breast cancer patients.

Figure 6:
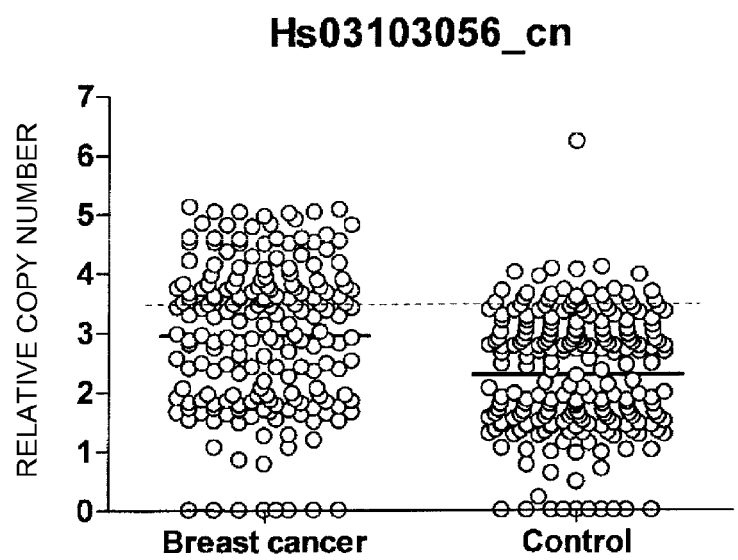
FIG. 6 is a diagram showing the results of the DNA copy number polymorphism detected by quantitative PCR with the primer set (Hs03103056_cn) in the group of healthy individuals (Control) and the group of breast cancer patients (Breast cancer). The horizontal line indicates the mean value in each group. The dotted line indicates the cut-off value. The symbol ○ indicates the number of copies in each individual.

[2] FIG. 6 and Table 7 (Hs03103056_cn): A DNA copy number of 3.5 or more in the chromosomal region (3q26.1 [163,706,172 to 163,706,287]), which is amplified by the primer set (Hs03103056_cn), was observed in 22 out of 216 individuals (10.2%) in the group of healthy individuals, whereas that was observed in 76 out of 193 individuals (39.4%) in the group of breast cancer patients, revealing a significantly high frequency of DNA copy number of 3.5 or more (P<0.0001, odds ratio of 5.7, Fisher's test) in the group of breast cancer patients.

Figure 7:
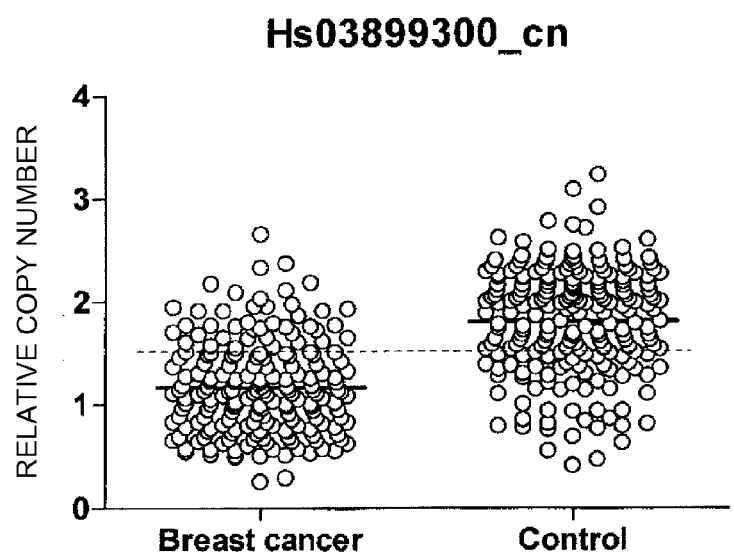
FIG. 7 is a diagram showing the results of the DNA copy number polymorphism detected by quantitative PCR with the primer set (Hs03899300_cn) in the group of healthy individuals (Control) and the group of breast cancer patients (Breast cancer). The horizontal line indicates the mean value in each group. The dotted line indicates the cut-off value. The symbol ○ indicates the number of copies in each individual.

[3] FIG. 7 and Table 7 (Hs03899300_cn): A DNA copy number of less than 1.5 in the chromosomal region (15q26.3 [99,845,920 to 99,846,025]), which is amplified by the primer set (Hs03899300_cn), was observed in 56 out of 216 individuals (25.9%) in the group of healthy individuals, whereas that was observed in 148 out of 193 individuals (76.7%) in the group of breast cancer patients, revealing a significantly high frequency of DNA copy number of less than 1.5 (P<0.0001, odds ratio of 9.4, Fisher's test) in the group of breast cancer patients.

Figure 8:
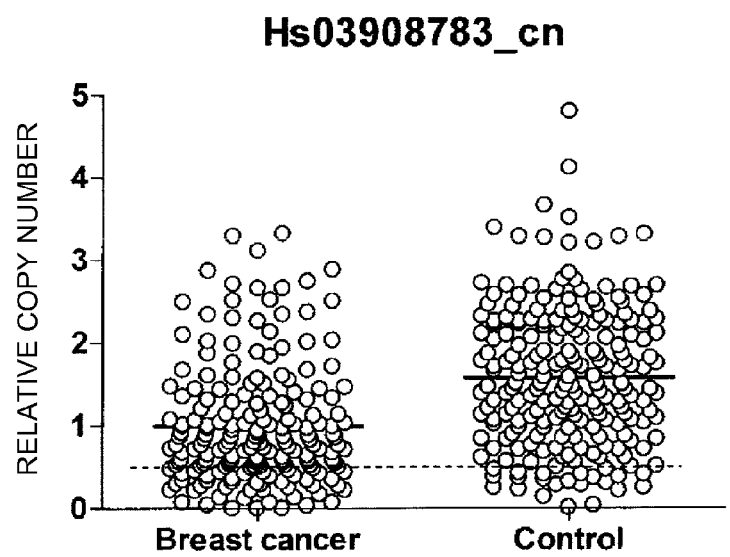
FIG. 8 is a diagram showing the results of the DNA copy number polymorphism detected by quantitative PCR with the primer set (Hs03908783_cn) in the group of healthy individuals (Control) and the group of breast cancer patients (Breast cancer). The horizontal line indicates the mean value in each group. The dotted line indicates the cut-off value. The symbol ○ indicates the number of copies in each individual.

[4] FIG. 8 and Table 7 (Hs03908783_cn): A DNA copy number of less than 0.5 in the chromosomal region (15q26.3 [99,847,947 to 99,848,043]), which is amplified by the primer set (Hs03908783_cn), was observed in 22 out of 216 individuals (10.2%) in the group of healthy individuals, whereas that was observed in 46 out of 193 individuals (23.8%) in the group of breast cancer patients, revealing a significantly high frequency of DNA copy number of less than 0.5 (P=0.0003, odds ratio of 2.8, Fisher's test) in the group of breast cancer patients.

Figure 9:
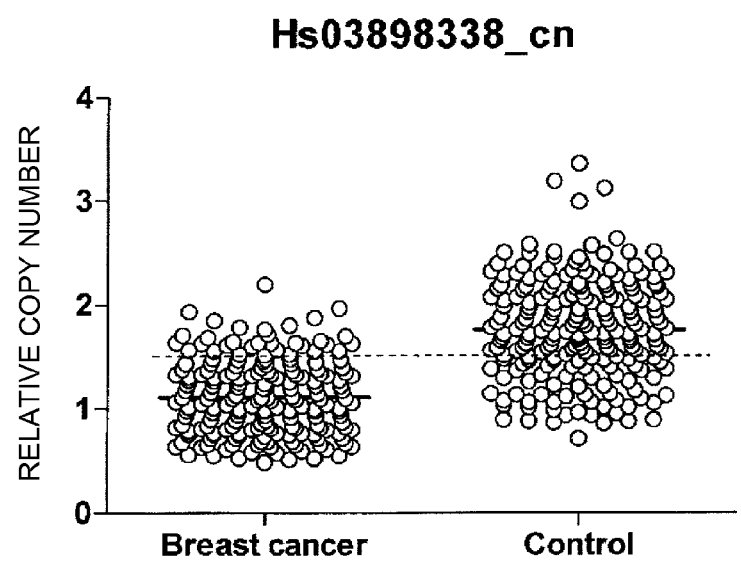
FIG. 9 is a diagram showing the results of the DNA copy number polymorphism detected by quantitative PCR with the primer set (Hs03898338_cn) in the group of healthy individuals (Control) and the group of breast cancer patients (Breast cancer). The horizontal line indicates the mean value in each group. The dotted line indicates the cut-off value. The symbol ○ indicates the number of copies in each individual.

[5] FIG. 9 and Table 7 (Hs03898338_cn): A DNA copy number of less than 1.5 in the chromosomal region (15q26.3 [99,848,547 to 99,848,623]), which is amplified by the primer set (Hs03898338_cn), was observed in 64 out of 216 individuals (29.6%) in the group of healthy individuals, whereas that was observed in 161 out of 193 individuals (83.4%) in the group of breast cancer patients, revealing a significantly high frequency of DNA copy number of less than 1.5 (P<0.0001, odds ratio of 11.9, Fisher's test) in the group of breast cancer patients.

Figure 10:
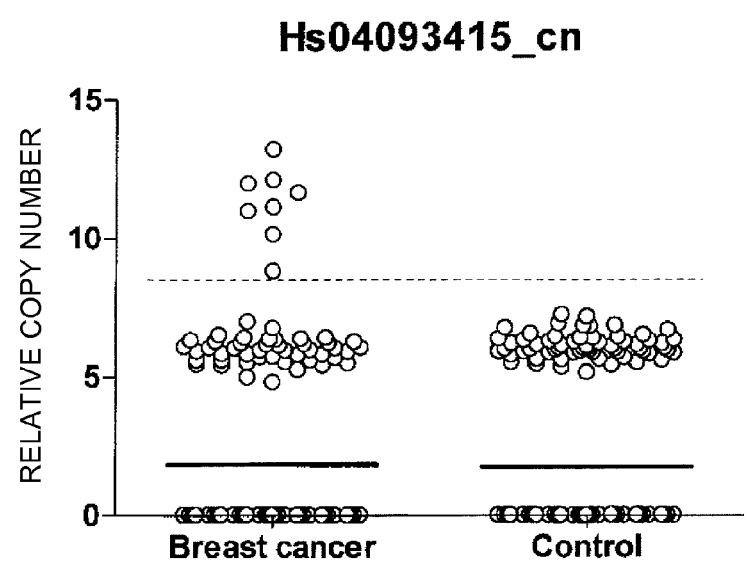
FIG. 10 is a diagram showing the results of the DNA copy number polymorphism detected by quantitative PCR with the primer set (Hs04093415_cn) in the group of healthy individuals (Control) and the group of breast cancer patients (Breast cancer). The horizontal line indicates the mean value in each group. The dotted line indicates the cut-off value. The symbol ○ indicates the number of copies in each individual.

[6] FIG. 10 and Table 7 (Hs04093415_cn): A DNA copy number of 9.0 or more in the chromosomal region (22q12.3 [35,473,730 to 35,473,804]), which is amplified by the primer set (Hs04093415_cn), was observed in 0 out of 216 individuals (0.0%) in the group of healthy individuals, whereas that was observed in 8 out of 193 individuals (4.1%) in the group of breast cancer patients, revealing a significantly high frequency of DNA copy number of 9.0 or more (P=0.0023, odds ratio of 19.8, Fisher's test) in the group of breast cancer patients.

Figure 11:
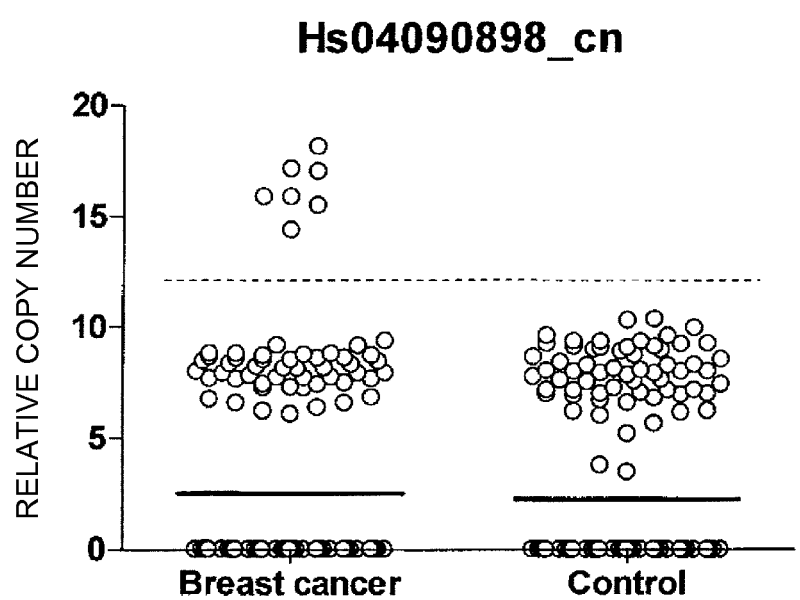
FIG. 11 is a diagram showing the results of the DNA copy number polymorphism detected by quantitative PCR with the primer set (Hs04090898_cn) in the group of healthy individuals (Control) and the group of breast cancer patients (Breast cancer). The horizontal line indicates the mean value in each group. The dotted line indicates the cut-off value. The symbol ○ indicates the number of copies in each individual.

[7] FIG. 11 and Table 7 (Hs04090898_cn): A DNA copy number of 12.0 or more in the chromosomal region (22q12.3 [35,475,937 to 35,476,043]), which is amplified by the primer set (Hs04090898_cn), was observed in 0 out of 216 individuals (0.0%) in the group of healthy individuals, whereas that was observed in 7 out of 193 individuals (3.6%) in the group of breast cancer patients, revealing a significantly high frequency of DNA copy number of 12.0 or more (P=0.0049, odds ratio of 17.4, Fisher's test) in the group of breast cancer patients.

From the analytical results of the quantitative PCR as described in [1] to [7] above, a breast cancer patient was successfully determined as positive with significance in the group of breast cancer patients than in a group of healthy individuals by setting a cut-off value (a value set for determining if an individual is a breast cancer patient or a healthy individual). The above results revealed that an individual having a DNA copy number polymorphism in the aforementioned seven regions can be determined as highly susceptible to breast cancer.

(2) Discriminant Analysis

From among the aforementioned seven regions, in which the DNA copy number was measured by quantitative PCR, various combination patterns of two regions were selected, and discriminant analyses were performed. The results are shown in FIGS. 12 to 32 and Table 8.

Figure 12:
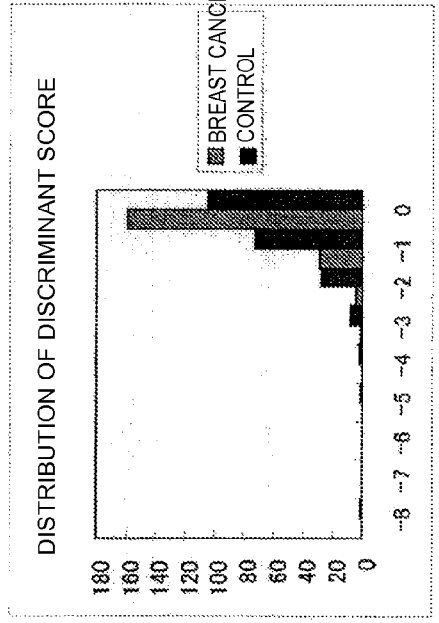
FIG. 12 is a diagram showing the results of the discriminant analysis performed based on the results obtained in FIGS. 5 and 10.
Figure 12:
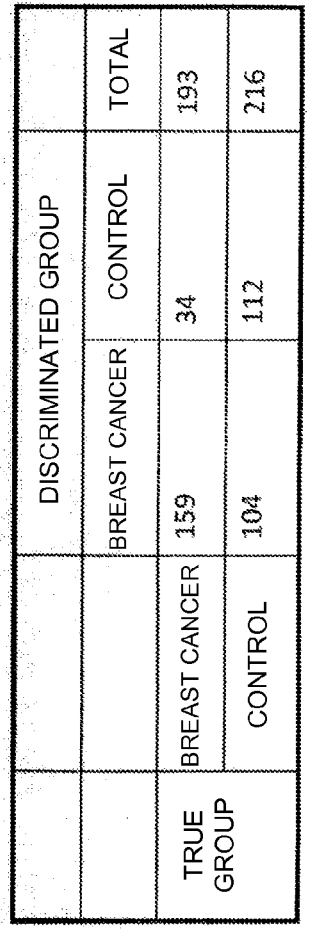

[1] FIG. 12 and Table 8 (a combination of Hs06535529_cn and Hs04093415_cn): A discriminant analysis was performed based on the results obtained in FIG. 5 and FIG. 10. In the analysis, a discriminant score Y can be obtained by using the linear discriminant formula (Y=[Hs06535529_cn copy number]×(−0.5695)+[Hs04093415_cn copy number]×(0.0236)+(0.7142). When a discriminant score of 0 or more was determined as susceptible to breast cancer and a discriminant score of less than 0 was determined as not susceptible to breast cancer, among 193 true breast cancer patients, 159 individuals were determined as "having breast cancer" (a discriminant score of 0 or more) (sensitivity: 82.4%) by the above discriminant formula, while among 216 true healthy individuals, 112 individuals were determined as "not having breast cancer" (a discriminant score of less than 0) (specificity: 51.9%). It is to be noted that the term "Hs06535529_cn copy number" refers to the number of copies of a chromosomal region amplified by the primer set (Hs06535529_cn), that is, the number of copies of "1p36.12 (21,375,430 to 21,375,511)". Also, the terms "Hs04093415_cn copy number" refers to the number of copies of a chromosomal region amplified by the primer set (Hs04093415_cn), that is, the number of copies of "22q12.3 (35,473,730 to 35,473,804)".

Figure 13:
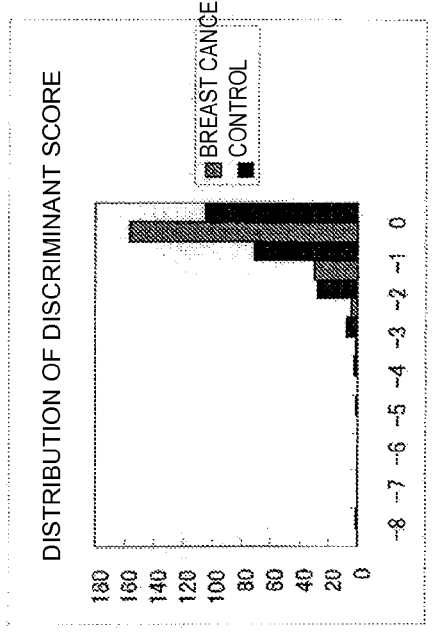
FIG. 13 is a diagram showing the results of the discriminant analysis performed based on the results obtained in FIGS. 5 and 11.

[2] FIG. 13 and Table 8 (a combination of Hs06535529_cn and Hs04090898_cn): A discriminant analysis was performed based on the results obtained in FIG. 5 and FIG. 11. In the analysis, a discriminant score Y can be obtained by using the linear discriminant formula (Y=[Hs06535529_cn copy number]×(−0.5699)+[Hs04090898_cn copy number]×(0.0252)+(0.697). When a discriminant score of 0 or more was determined as susceptible to breast cancer and a discriminant score of less than 0 was determined as not susceptible to breast cancer, among 193 true breast cancer patients, 158 individuals were determined as "having breast cancer" (a discriminant score of 0 or more) (sensitivity: 81.9%) by the above discriminant formula, while among 216 true healthy individuals, 111 individuals were determined as "not having breast cancer" (a discriminant score of less than 0) (specificity: 51.4%). It is to be noted that the term "Hs06535529_cn copy number" is as explained above and the term "Hs04090898_cn copy number" refers to the number of copies of a chromosomal region amplified by the primer set (Hs04090898_cn), that is, the number of copies of "22q12.3 (35, 475, 937 to 35,476,043)."

Figure 14:
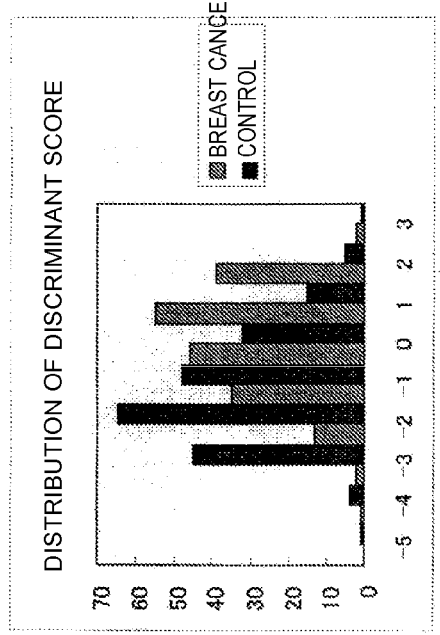
FIG. 14 is a diagram showing the results of the discriminant analysis performed based on the results obtained in FIGS. 5 and 7.

[3] FIG. 14 and Table 8 (a combination of Hs06535529_cn and Hs03899300_cn): A discriminant analysis was performed based on the results obtained in FIG. 5 and FIG. 7. In the analysis, a discriminant score Y can be obtained by using the linear discriminant formula (Y= [Hs06535529_cn copy number]×(0.1403)+ [Hs03899300_cn copy number]×(−2.9466)+(4.2074). When a discriminant score of 0 or more was determined as susceptible to breast cancer and a discriminant score of less than 0 was determined as not susceptible to breast cancer, among 193 true breast cancer patients, 142 individuals were determined as "having breast cancer" (a discriminant score of 0 or more) (sensitivity: 73.6%) by the above discriminant formula, while among 216 true healthy individuals, 163 individuals were determined as "not having breast cancer" (a discriminant score of less than 0) (specificity: 75.5%). It is to be noted that the term "Hs06535529_cn copy number" is as explained above and the term "Hs03899300_cn copy number" refers to the number of copies of a chromosomal region amplified by the primer set (Hs03899300_cn), that is, the number of copies of "15q26.3 (99, 845, 920 to 99,846,025)."

Figure 15:
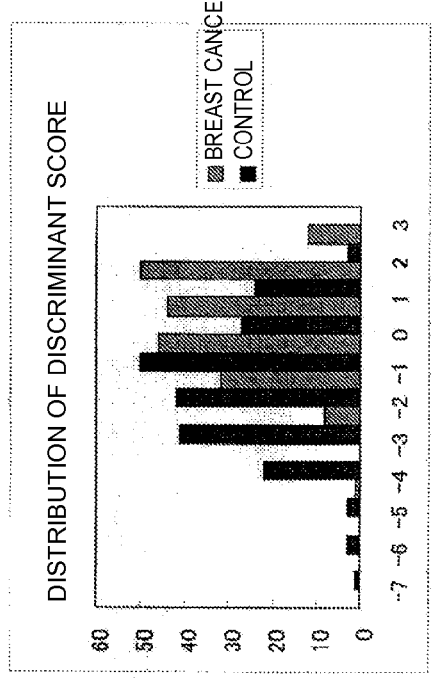
FIG. 15 is a diagram showing the results of the discriminant analysis performed based on the results obtained in FIGS. 5 and 9.

[4] FIG. 15 and Table 8 (a combination of Hs06535529_cn and Hs03898338_cn): A discriminant analysis was performed based on the results obtained in FIG. 5 and FIG. 9. In the analysis, a discriminant score Y can be obtained by using the linear discriminant formula (Y= [Hs06535529_cn copy number]×(0.1399)+ [Hs03898338_cn copy number]×(−3.7991)+(5.2721). When a discriminant score of 0 or more was determined as susceptible to breast cancer and a discriminant score of less than 0 was determined as not susceptible to breast cancer, among 193 true breast cancer patients, 152 individuals were determined as "having breast cancer" (a discriminant score of 0 or more) (sensitivity: 78.8%) by the above discriminant formula, while among 216 true healthy individuals, 162 individuals were determined as "not having breast cancer" (a discriminant score of less than 0) (specificity: 75.0%). It is to be noted that the term "Hs06535529_cn copy number" is as explained above and the term "Hs03898338_cn copy number" refers to the number of copies of a chromosomal region amplified by the primer set (Hs03898338_cn), that is, the number of copies of "15q26.3 (99,848,547 to 99,848,623)."

Figure 16:
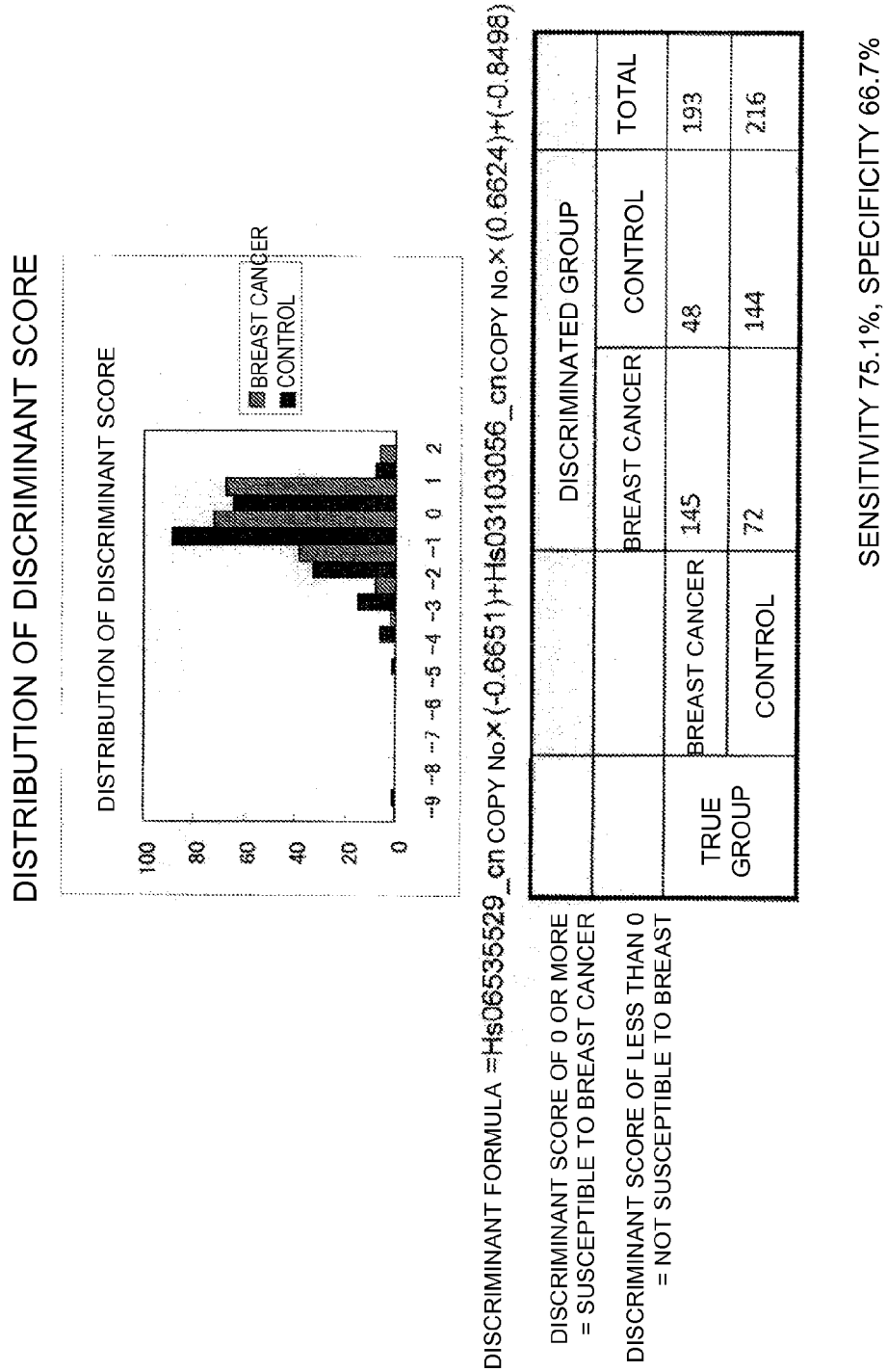
FIG. 16 is a diagram showing the results of the discriminant analysis performed based on the results obtained in FIGS. 5 and 6.

[5] FIG. 16 and Table 8 (a combination of Hs06535529_cn and Hs03103056_cn): A discriminant analysis was performed based on the results obtained in FIG. 5 and FIG. 6. In the analysis, a discriminant score Y can be obtained by using the linear discriminant formula (Y= [Hs06535529_cn copy number]×(−0.6651)+ [Hs03103056_cn copy number]×(0.6624)+(−0.8498). When a discriminant score of 0 or more was determined as susceptible to breast cancer and a discriminant score of less than 0 was determined as not susceptible to breast cancer, among 193 true breast cancer patients, 145 individuals were determined as "having breast cancer" (a discriminant score of 0 or more) (sensitivity: 75.1%) by the above discriminant formula, while among 216 true healthy individuals, 144 individuals were determined as "not having breast cancer" (a discriminant score of less than 0) (specificity: 66.7%). It is to be noted that the term "Hs06535529_cn copy number" is as explained above and the term "Hs03103056_cn copy number" refers to the number of copies of a chromosomal region amplified by the primer set (Hs03103056_cn), that is, the number of copies of "3q26.1 (163, 706, 172 to 163,706,287)."

Figure 17:
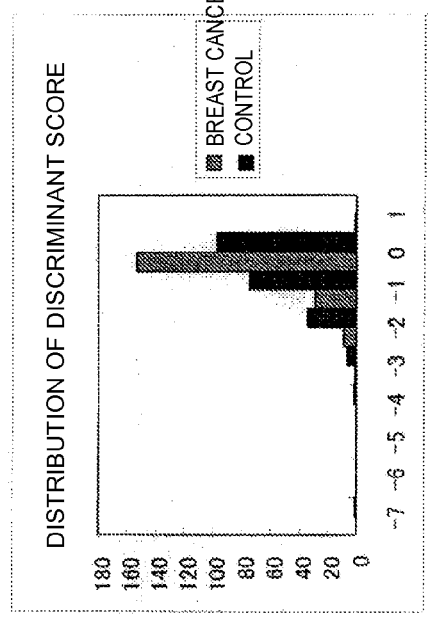
FIG. 17 is a diagram showing the results of the discriminant analysis performed based on the results obtained in FIGS. 5 and 8.

[6] FIG. 17 and Table 8 (a combination of Hs06535529_cn and Hs03908783_cn): A discriminant analysis was performed based on the results obtained in FIG. 5 and FIG. 8. In the analysis, a discriminant score Y can be obtained by using the linear discriminant formula (Y= [Hs06535529_cn copy number]×(−0.3911)+ [Hs03908783_cn copy number]×(−0.3972)+(1.0298). When a discriminant score of 0 or more was determined as susceptible to breast cancer and a discriminant score of less than 0 was determined as not susceptible to breast cancer, among 193 true breast cancer patients, 154 individuals were determined as "having breast cancer" (a discriminant score of 0 or more) (sensitivity: 79.8%) by the above discriminant formula, while among 216 true healthy individuals, 119 individuals were determined as "not having breast cancer" (a discriminant score of less than 0) (specificity: 55.1%). It is to be noted that the term "Hs06535529_cn copy number" is as explained above and the term "Hs03908783_cn copy number" refers to the number of copies of a chromosomal region amplified by the primer set (Hs03908783_cn), that is, the number of copies of "15q26.3 (99,847,947 to 99,848,043)."

Figure 18:
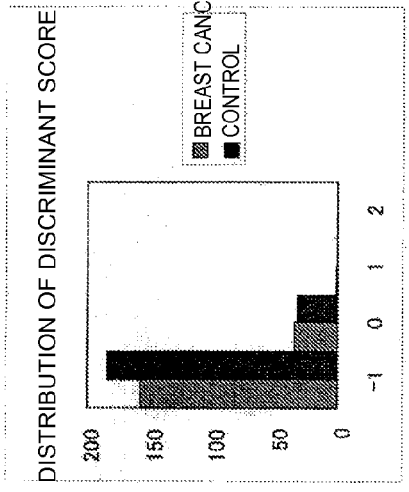
FIG. 18 is a diagram showing the results of the discriminant analysis performed based on the results obtained in FIGS. 10 and 11.

[7] FIG. 18 and Table 8 (a combination of Hs04093415_cn and Hs04090898_cn): A discriminant analysis was performed based on the results obtained in FIG. 10 and FIG. 11. In the analysis, a discriminant score Y can be obtained by using the linear discriminant formula (Y= [Hs04093415_cn copy number]×(−0.2285)+ [Hs04090898_cn copy number]×(0.1834)+(−0.0272). When a discriminant score of 0 or more was determined as susceptible to breast cancer and a discriminant score of less than 0 was determined as not susceptible to breast cancer, among 193 true breast cancer patients, 35 individuals were determined as "having breast cancer" (a discriminant score of 0 or more) (sensitivity: 18.1%) by the above discriminant formula, while among 216 true healthy individuals, 184 individuals were determined as "not having breast cancer" (a discriminant score of less than 0) (specificity: 85.2%). Also, the term "Hs04093415_cn copy number" is as explained above and the term "Hs04090898_cn copy number" is as explained above.

Figure 19:
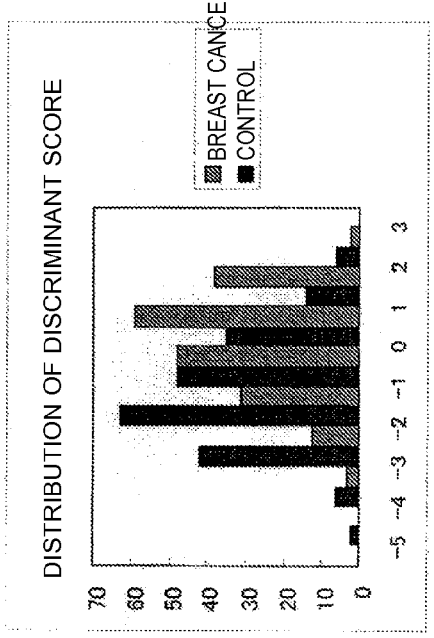
FIG. 19 is a diagram showing the results of the discriminant analysis performed based on the results obtained in FIGS. 7 and 10.

[8] FIG. 19 and Table 8 (a combination of Hs04093415_cn and Hs03899300_cn): A discriminant analysis was performed based on the results obtained in FIG. 7 and FIG. 10. In the analysis, a discriminant score Y can be obtained by using the linear discriminant formula (Y= [Hs04093415_cn copy number]×(0.0423)+ [Hs03899300_cn copy number]×(−2.6949)+(3.9423). When a discriminant score of 0 or more was determined as susceptible to breast cancer and a discriminant score of less than 0 was determined as not susceptible to breast cancer, among 193 true breast cancer patients, 147 individuals were determined as "having breast cancer" (a discriminant score of 0 or more) (sensitivity: 76.2%) by the above discriminant formula, while among 216 true healthy individuals, 161 individuals were determined as "not having breast cancer" (a discriminant score of less than 0) (specificity: 74.5%). Also, the term "Hs04093415_cn copy number" is as explained above and the term "Hs03899300_cn copy number" is as explained above.

Figure 20:
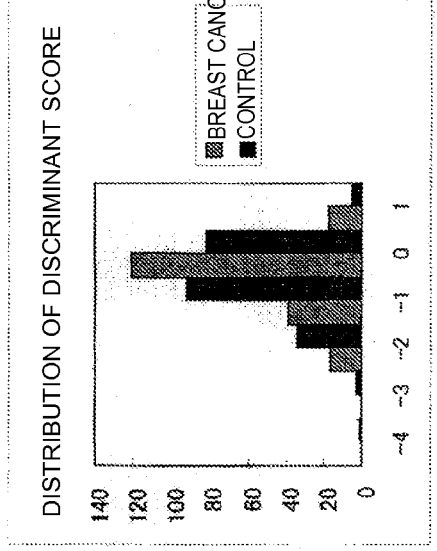
FIG. 20 is a diagram showing the results of the discriminant analysis performed based on the results obtained in FIGS. 8 and 10.

[9] FIG. 20 and Table 8 (a combination of Hs04093415_cn and Hs03908783_cn): A discriminant analysis was performed based on the results obtained in FIG. 8 and FIG. 10. In the analysis, a discriminant score Y can be obtained by using the linear discriminant formula (Y= [Hs04093415_cn copy number]×(0.0316)+ [Hs03908783_cn copy number]×(−0.9415)+(1.1523). When a discriminant score of 0 or more was determined as susceptible to breast cancer and a discriminant score of less than 0 was determined as not susceptible to breast cancer, among 193 true breast cancer patients, 138 individuals were determined as "having breast cancer" (a discriminant score of 0 or more) (sensitivity: 71.5%) by the above discriminant formula, while among 216 true healthy individuals, 130 individuals were determined as "not having breast cancer" (a discriminant score of less than 0) (specificity: 60.2%). Also, the term "Hs04093415_cn copy number" is as explained above and the term "Hs03908783_cn copy number" is as explained above.

Figure 21:
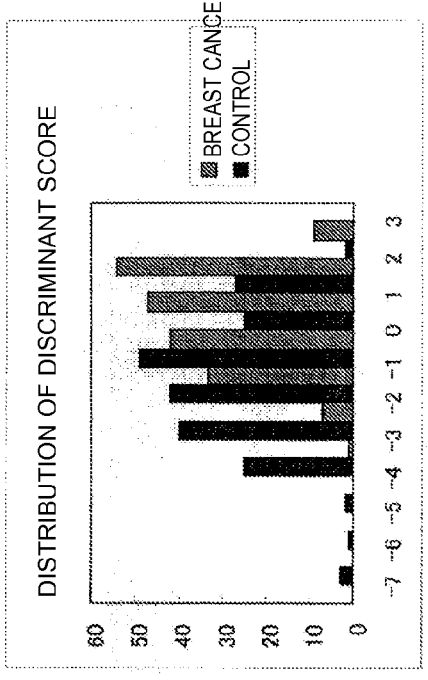
FIG. 21 is a diagram showing the results of the discriminant analysis performed based on the results obtained in FIGS. 9 and 10.

[10] FIG. 21 and Table 8 (a combination of Hs04093415_cn and Hs03898338_cn): A discriminant analysis was performed based on the results obtained in FIG. 9 and FIG. 10. In the analysis, a discriminant score Y can be obtained by using the linear discriminant formula (Y= [Hs04093415_cn copy number]×(0.0342)+ [Hs03898338_cn copy number]×(−3.5383)+(5.0218). When a discriminant score of 0 or more was determined as susceptible to breast cancer and a discriminant score of less than 0 was determined as not susceptible to breast cancer, among 193 true breast cancer patients, 152 individuals were determined as "having breast cancer" (a discriminant score of 0 or more) (sensitivity: 78.8%) by the above discriminant formula, while among 216 true healthy individuals, 162 individuals were determined as "not having breast cancer" (a discriminant score of less than 0) (specificity: 75.0%). Also, the term "Hs04093415_cn copy number" is as explained above and the term "Hs03898338_cn copy number" is as explained above.

Figure 22:
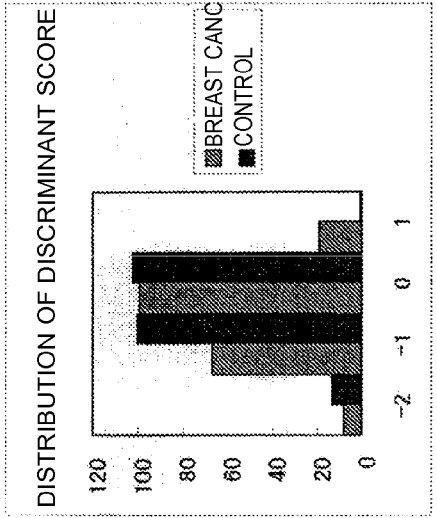
FIG. 22 is a diagram showing the results of the discriminant analysis performed based on the results obtained in FIGS. 6 and 10.

[11] FIG. 22 and Table 8 (a combination of Hs04093415_cn and Hs03103056_cn): A discriminant analysis was performed based on the results obtained in FIG. 6 and FIG. 10. In the analysis, a discriminant score Y can be obtained by using the linear discriminant formula (Y= [Hs04093415_cn copy number]×(0.005)+ [Hs03103056_cn copy number]×(0.5142)+(−1.3547). When a discriminant score of 0 or more was determined as susceptible to breast cancer and a discriminant score of less than 0 was determined as not susceptible to breast cancer, among 193 true breast cancer patients, 118 individuals were determined as "having breast cancer" (a discriminant score of 0 or more) (sensitivity: 61.1%) by the above discriminant formula, while among 216 true healthy individuals, 113 individuals were determined as "not having breast cancer" (a discriminant score of less than 0) (specificity: 52.3%). Also, the term "Hs04093415_cn copy number" is as explained above and the term "Hs03103056_cn copy number" is as explained above.

Figure 23:
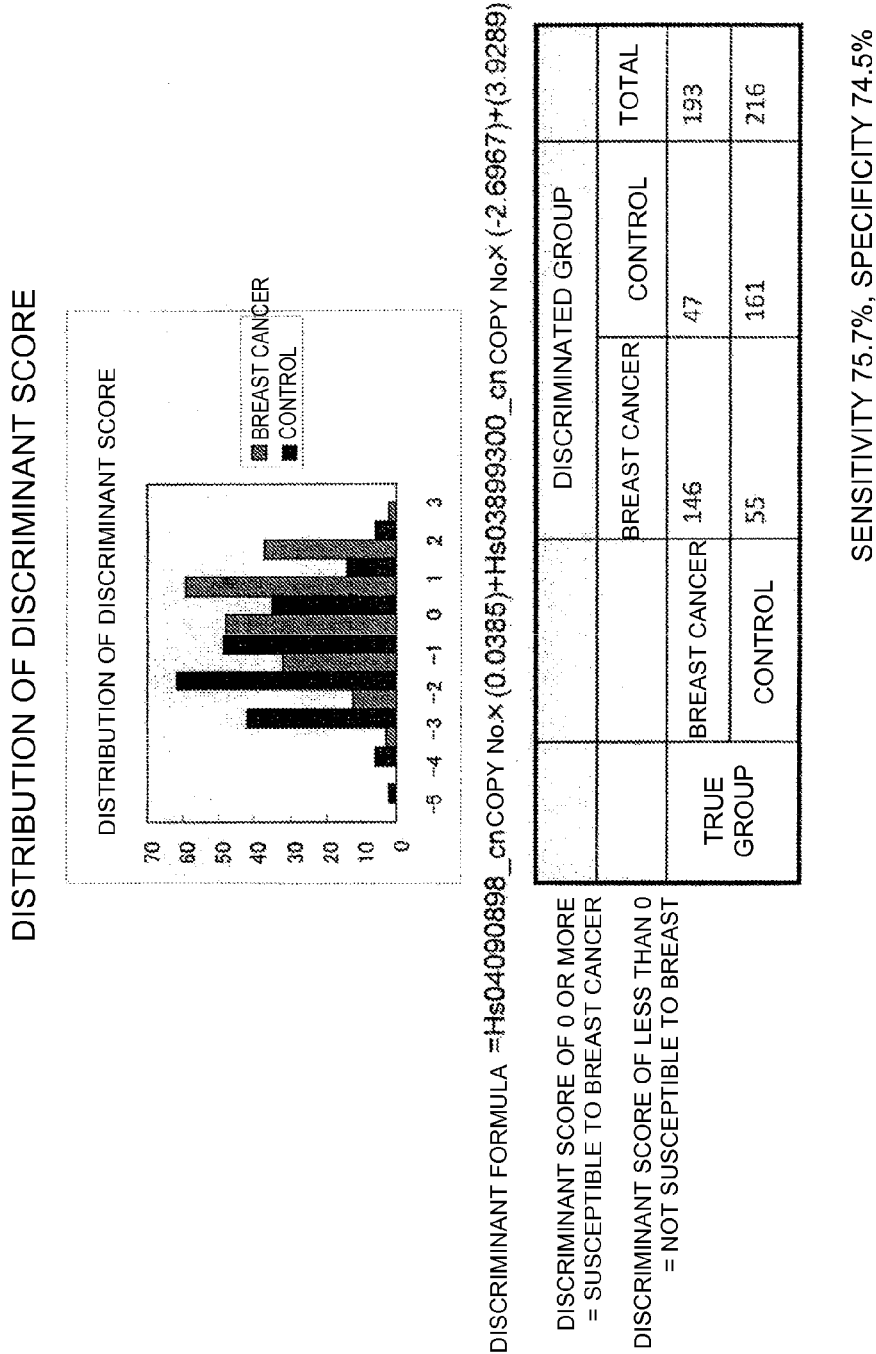
FIG. 23 is a diagram showing the results of the discriminant analysis performed based on the results obtained in FIGS. 7 and 11.

[12] FIG. 23 and Table 8 (a combination of Hs04090898_cn and Hs03899300_cn): A discriminant analysis was performed based on the results obtained in FIG. 7 and FIG. 11. In the analysis, a discriminant score Y can be obtained by using the linear discriminant formula (Y= [Hs04090898_cn copy number]×(0.0385)+ [Hs03899300_cn copy number]×(−2.6967)+(3.9289). When a discriminant score of 0 or more was determined as susceptible to breast cancer and a discriminant score of less than 0 was determined as not susceptible to breast cancer, among 193 true breast cancer patients, 146 individuals were determined as "having breast cancer" (a discriminant score of 0 or more) (sensitivity: 75.7%) by the above discriminant formula, while among 216 true healthy individuals, 161 individuals were determined as "not having breast cancer" (a discriminant score of less than 0) (specificity: 74.5%). Also, the term "Hs04090898_cn copy number" is as explained above and the term "Hs03899300_cn copy number" is as explained above.

Figure 24:
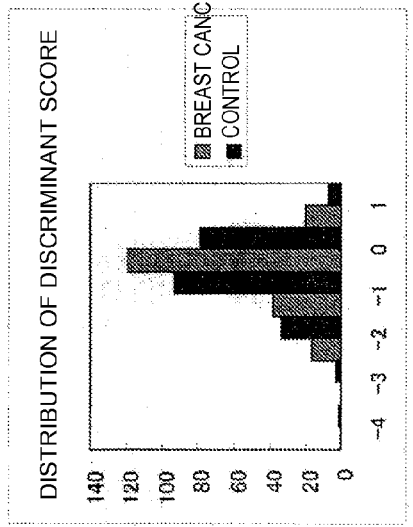
FIG. 24 is a diagram showing the results of the discriminant analysis performed based on the results obtained in FIGS. 8 and 11.

[13] FIG. 24 and Table 8 (a combination of Hs04090898_cn and Hs03908783_cn): A discriminant analysis was performed based on the results obtained in FIG. 8 and FIG. 11. In the analysis, a discriminant score Y can be obtained by using the linear discriminant formula (Y= [Hs04090898_cn copy number]×(0.031)+ [Hs03908783_cn copy number]×(−0.943)+(1.137). When a discriminant score of 0 or more was determined as susceptible to breast cancer and a discriminant score of less than 0 was determined as not susceptible to breast cancer, among 193 true breast cancer patients, 139 individuals were determined as "having breast cancer" (a discriminant score of 0 or more) (sensitivity: 72.0%) by the above discriminant formula, while among 216 true healthy individuals, 130 individuals were determined as "not having breast cancer" (a discriminant score of less than 0) (specificity: 60.2%). Also, the term "Hs04090898_cn copy number" is as explained above and the term "Hs03908783_cn copy number" is as explained above.

Figure 25:
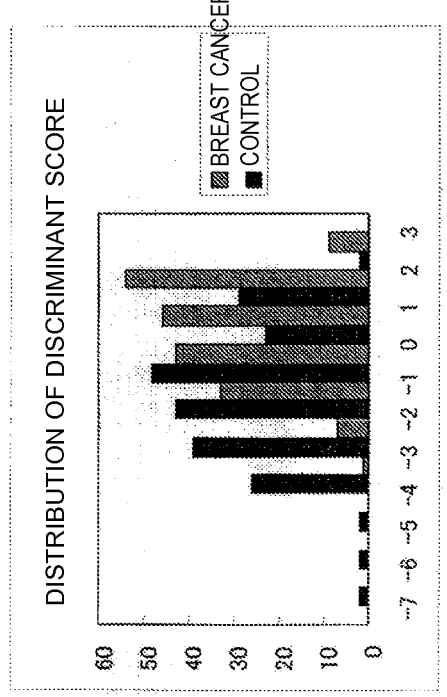
FIG. 25 is a diagram showing the results of the discriminant analysis performed based on the results obtained in FIGS. 9 and 11.

[14] FIG. 25 and Table 8 (a combination of Hs04090898_cn and Hs03898338_cn): A discriminant analysis was performed based on the results obtained in FIG. 9 and FIG. 11. In the analysis, a discriminant score Y can be obtained by using the linear discriminant formula (Y= [Hs04090898_cn copy number]×(0.0191)+ [Hs03898338_cn copy number]×(−3.5282)+(5.0233). When a discriminant score of 0 or more was determined as susceptible to breast cancer and a discriminant score of less than 0 was determined as not susceptible to breast cancer, among 193 true breast cancer patients, 152 individuals were determined as "having breast cancer" (a discriminant score of 0 or more) (sensitivity: 78.8%) by the above discriminant formula, while among 216 true healthy individuals, 162 individuals were determined as "not having breast cancer" (a discriminant score of less than 0) (specificity: 75.0%). Also, the term "Hs04090898_cn copy number" is as explained above and the term "Hs03898338_cn copy number" is as explained above.

Figure 26:
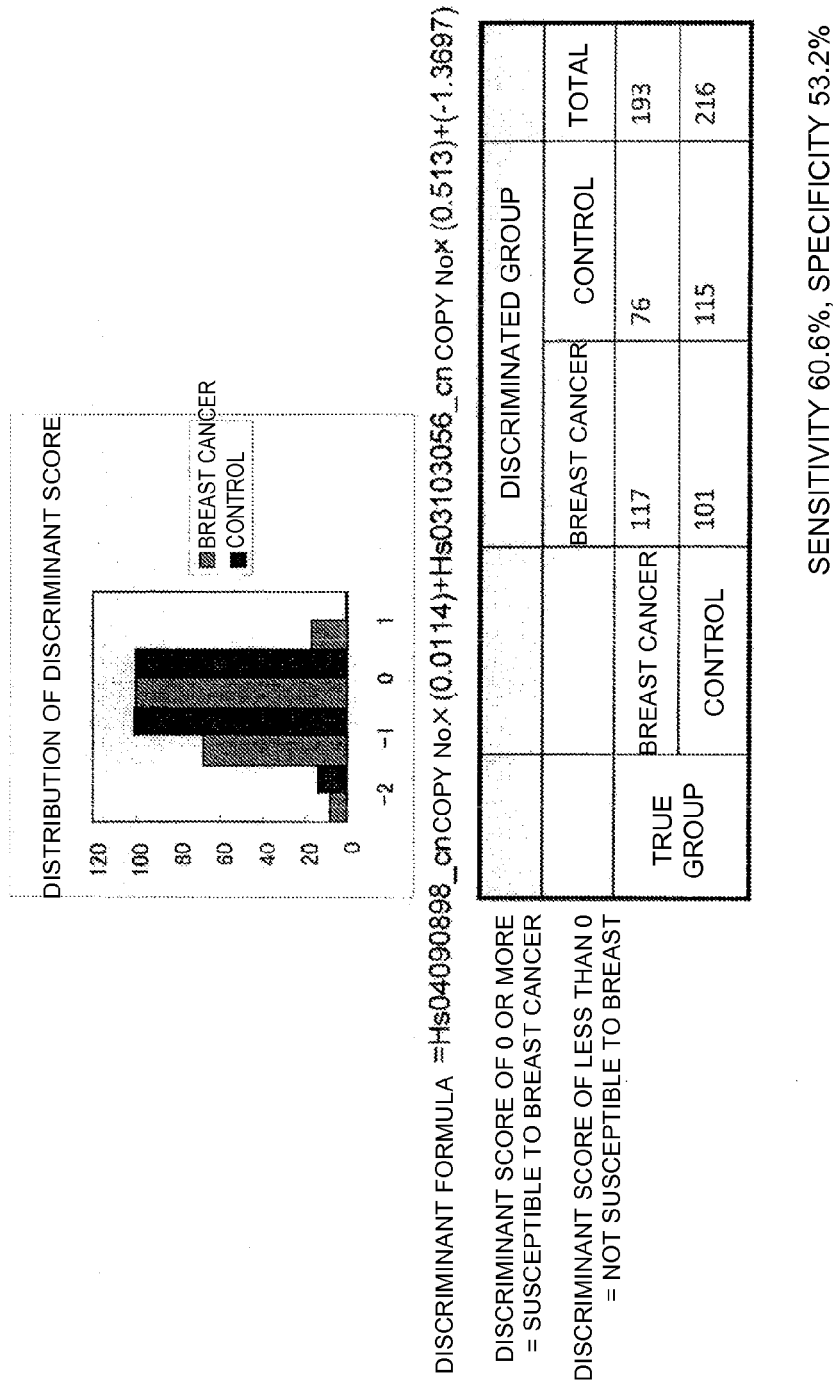
FIG. 26 is a diagram showing the results of the discriminant analysis performed based on the results obtained in FIGS. 6 and 11.

[15] FIG. 26 and Table 8 (a combination of Hs04090898_cn and Hs03103056_cn): A discriminant analysis was performed based on the results obtained in FIG. 6 and FIG. 11. In the analysis, a discriminant score Y can be obtained by using the linear discriminant formula (Y= [Hs04090898_cn copy number]×(0.0114)+ [Hs03103056_cn copy number]×(0.513)+(−1.3697). When a discriminant score of 0 or more was determined as susceptible to breast cancer and a discriminant score of less than 0 was determined as not susceptible to breast cancer, among 193 true breast cancer patients, 117 individuals were determined as "having breast cancer" (a discriminant score of 0 or more) (sensitivity: 60.6%) by the above discriminant formula, while among 216 true healthy individuals, 115 individuals were determined as "not having breast cancer" (a discriminant score of less than 0) (specificity: 53.2%). Also, the term "Hs04090898_cn copy number" is as explained above and the term "Hs03103056_cn copy number" is as explained above.

Figure 27:
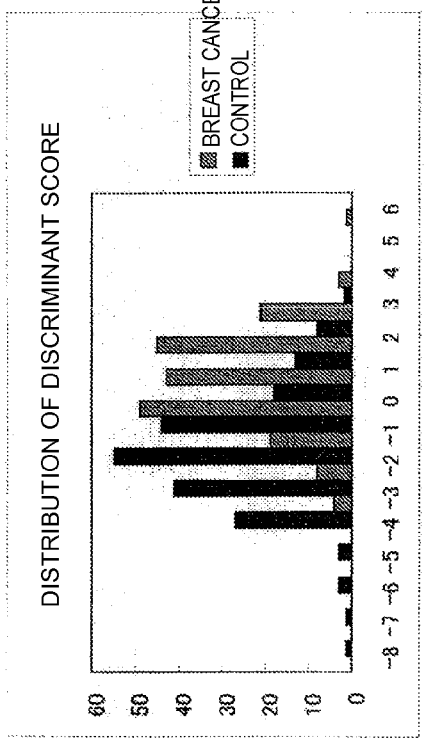
FIG. 27 is a diagram showing the results of the discriminant analysis performed based on the results obtained in FIGS. 7 and 8.

[16] FIG. 27 and Table 8 (a combination of Hs03899300_cn and Hs03908783_cn): A discriminant analysis was performed based on the results obtained in FIG. 7 and FIG. 8. In the analysis, a discriminant score Y can be obtained by using the linear discriminant formula (Y= [Hs03899300_cn copy number]×(−6.7554)+ [Hs03908783_cn copy number]×(2.823)+(6.4471). When a discriminant score of 0 or more was determined as susceptible to breast cancer and a discriminant score of less than 0 was determined as not susceptible to breast cancer, among 193 true breast cancer patients, 162 individuals were determined as "having breast cancer" (a discriminant score of 0 or more) (sensitivity: 83.9%) by the above discriminant formula, while among 216 true healthy individuals, 175 individuals were determined as "not having breast cancer" (a discriminant score of less than 0) (specificity: 81.0%). Also, the term "Hs03899300_cn copy number" is as explained above and the term "Hs03908783_cn copy number" is as explained above.

Figure 28:
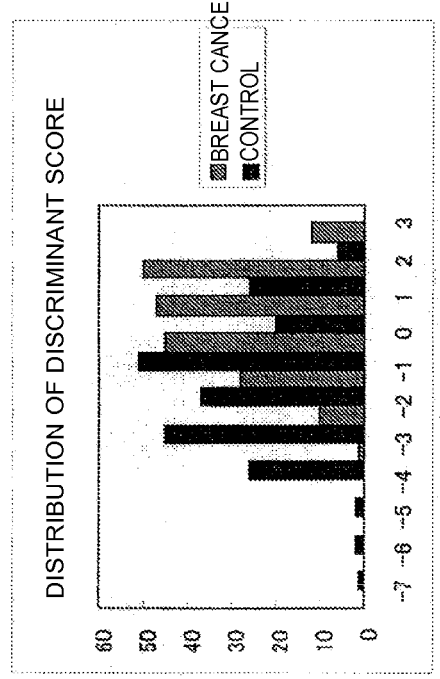
FIG. 28 is a diagram showing the results of the discriminant analysis performed based on the results obtained in FIGS. 7 and 9.

[17] FIG. 28 and Table 8 (a combination of Hs03899300_cn and Hs03898338_cn): A discriminant analysis was performed based on the results obtained in FIG. 7 and FIG. 9. In the analysis, a discriminant score Y can be obtained by using the linear discriminant formula (Y= [Hs03899300_cn copy number]×(−0.6719)+ [Hs03898338_cn copy number]×(−2.929)+(5.2098). When a discriminant score of 0 or more was determined as susceptible to breast cancer and a discriminant score of less than 0 was determined as not susceptible to breast cancer, among 193 true breast cancer patients, 154 individuals were determined as "having breast cancer" (a discriminant score of 0 or more) (sensitivity: 79.8%) by the above discriminant formula, while among 216 true healthy individuals, 164 individuals were determined as "not having breast cancer" (a discriminant score of less than 0) (specificity: 75.9%). Also, the term "Hs03899300_cn copy number" is as explained above and the term "Hs03898338_cn copy number" is as explained above.

Figure 29:
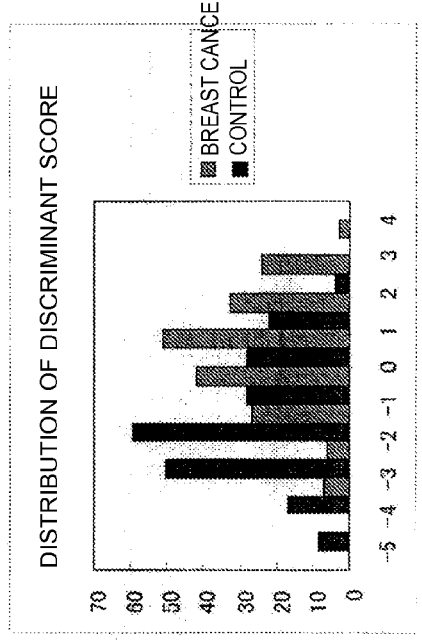
FIG. 29 is a diagram showing the results of the discriminant analysis performed based on the results obtained in FIGS. 6 and 7.

[18] FIG. 29 and Table 8 (a combination of Hs03899300_cn and Hs03103056_cn): A discriminant analysis was performed based on the results obtained in FIG. 6 and FIG. 7. In the analysis, a discriminant score Y can be obtained by using the linear discriminant formula (Y= [Hs03899300_cn copy number]×(−3.0532)+ [Hs03103056_cn copy number]×(0.7876)+(2.4915). When a discriminant score of 0 or more was determined as susceptible to breast cancer and a discriminant score of less than 0 was determined as not susceptible to breast cancer, among 193 true breast cancer patients, 153 individuals were determined as "having breast cancer" (a discriminant score of 0 or more) (sensitivity: 79.3%) by the above discriminant formula, while among 216 true healthy individuals, 162 individuals were determined as "not having breast cancer" (a discriminant score of less than 0) (specificity: 75.0%). Also, the term "Hs03899300_cn copy number" is as explained above and the term "Hs03103056_cn copy number" is as explained above.

Figure 30:
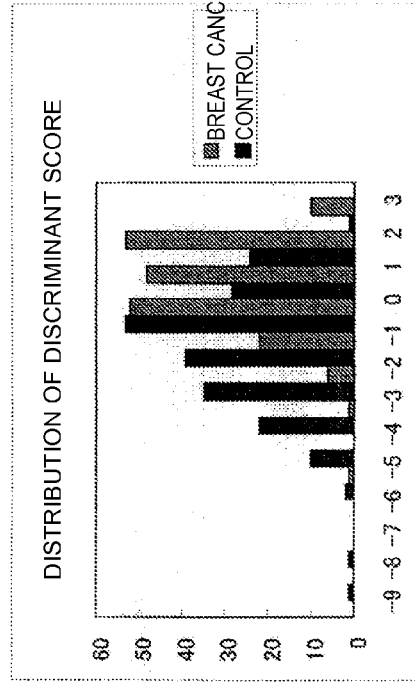
FIG. 30 is a diagram showing the results of the discriminant analysis performed based on the results obtained in FIGS. 8 and 9.

[19] FIG. 30 and Table 8 (a combination of Hs03908783_cn and Hs03898338_cn): A discriminant analysis was performed based on the results obtained in FIG. 8 and FIG. 9. In the analysis, a discriminant score Y can be obtained by using the linear discriminant formula (Y= [Hs03908783_cn copy number]×(0.7877)+ [Hs03898338_cn copy number]×(−4.5371)+(5.5065). When a discriminant score of 0 or more was determined as susceptible to breast cancer and a discriminant score of less than 0 was determined as not susceptible to breast cancer, among 193 true breast cancer patients, 163 individuals were determined as "having breast cancer" (a discriminant score of 0 or more) (sensitivity: 84.5%) by the above discriminant formula, while among 216 true healthy individuals, 163 individuals were determined as "not having breast cancer" (a discriminant score of less than 0) (specificity: 75.5%). Also, the term "Hs03908783_cn copy number" is as explained above and the term "Hs03898338_cn copy number" is as explained above.

Figure 31:
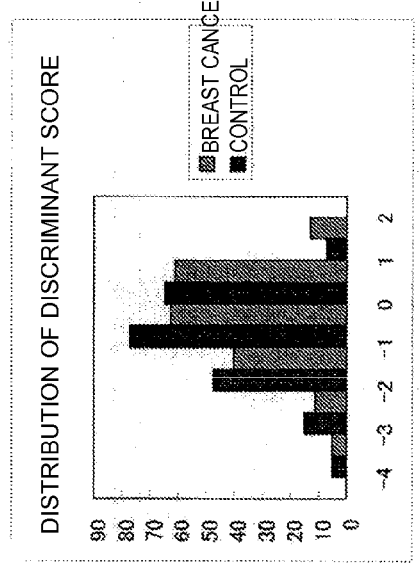
FIG. 31 is a diagram showing the results of the discriminant analysis performed based on the results obtained in FIGS. 6 and 8.

[20] FIG. 31 and Table 8 (a combination of Hs03908783_cn and Hs03103056_cn): A discriminant analysis was performed based on the results obtained in FIG. 6 and FIG. 8. In the analysis, a discriminant score Y can be obtained by using the linear discriminant formula (Y= [Hs03908783_cn copy number]×(−1.1372)+ [Hs03103056_cn copy number]×(0.6815)+(−0.3227). When a discriminant score of 0 or more was determined as susceptible to breast cancer and a discriminant score of less than 0 was determined as not susceptible to breast cancer, among 193 true breast cancer patients, 137 individuals were determined as "having breast cancer" (a discriminant score of 0 or more) (sensitivity: 71.0%) by the above discriminant formula, while among 216 true healthy individuals, 144 individuals were determined as "not having breast cancer" (a discriminant score of less than 0) (specificity: 66.7%). Also, the term "Hs03908783_cn copy number" is as explained above and the term "Hs03103056_cn copy number" is as explained above.

Figure 32:
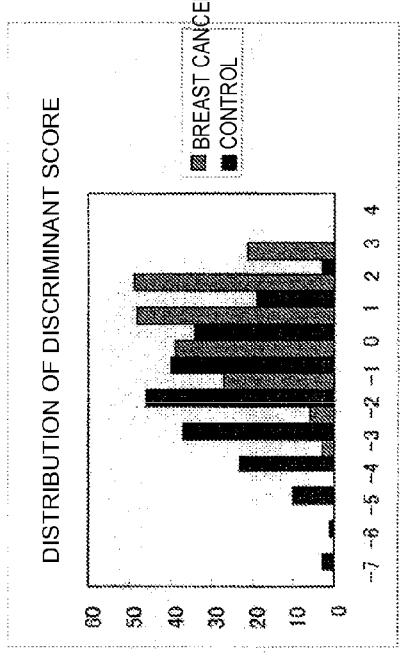
FIG. 32 is a diagram showing the results of the discriminant analysis performed based on the results obtained in FIGS. 6 and 9.

[21] FIG. 32 and Table 8 (a combination of Hs03898338_cn and Hs03103056_cn): A discriminant analysis was performed based on the results obtained in FIG. 6 and FIG. 9. In the analysis, a discriminant score Y can be obtained by using the linear discriminant formula (Y= [Hs03898338_cn copy number]×(−3.4991)+ [Hs03103056_cn copy number]×(0.4852)+(3.7572). When a discriminant score of 0 or more was determined as susceptible to breast cancer and a discriminant score of less than 0 was determined as not susceptible to breast cancer, among 193 true breast cancer patients, 157 individuals were determined as "having breast cancer" (a discriminant score of 0 or more) (sensitivity: 81.4%) by the above discriminant formula, while among 216 true healthy individuals, 160 individuals were determined as "not having breast cancer" (a discriminant score of less than 0) (specificity: 74.1%). Also, the term "Hs03898338_cn copy number" is as explained above and the term "Hs03103056_cn copy number" is as explained above.

From the results of the discriminant analyses [1] to [21] described above, focusing on sensitivity and specificity, a discriminant analysis shown in [16], namely a discriminant analysis performed on a combination of the chromosomal region (15q26.3 [99,845,920 to 99,846,025]) amplified by the primer set (Hs03899300_cn) and the chromosomal region (15q26.3 [99,847,947 to 99,848,043]) amplified by the primer set (Hs03908783_cn) was found to give the best results (sensitivity: 83.9%, specificity: 81.0%). Further, a discriminant analysis was performed with a combination of seven primer sets (Hs06535529_cn, Hs03103056_cn, Hs03899300_cn, Hs03908783_cn, Hs03898338_cn, Hs04093415_cn, and Hs04090898_cn). In the analysis, a discriminant score Y can be obtained by using the linear discriminant formula (Y=[Hs06535529_cn copy number]× (−0.4128)+[Hs04093415_cn copy number]×(0.02)+ [Hs04090898_cn copy number]×(−0.001)+[Hs03899300_cn copy number]×(−5.6747)+[Hs03908783_cn copy number]× (3.311)+[Hs03898338_cn copy number]×(−1.8864)+ [Hs03103056_cn copy number]×(0.6107)+(5.8360). When a discriminant score of 0 or more was determined as susceptible to breast cancer and a discriminant score of less than 0 was determined as not susceptible to breast cancer, among 193 true breast cancer patients, 172 individuals were determined as "having breast cancer" (a discriminant score of 0 or more) (sensitivity: 89.1%) by the above discriminant formula, while among 216 true healthy individuals, 171 individuals were determined as "not having breast cancer" (a discriminant score of less than 0) (specificity: 79.2%). These results indicate that although a healthy individual and a breast cancer patient can be discriminated from each other with significant difference by the aforementioned combination of seven primer sets, they can still be sufficiently discriminated from each other by a combination of two primer sets demonstrated in the aforementioned [16].

TABLE 7

| Copy number assay ® ID | Cut-off value | Number of breast cancer patients (Frequency) | Number of healthy individuals (Frequency) | Odds ratio | P Value |
| --- | --- | --- | --- | --- | --- |
| Hs06535529_cn | less than 0.5 | 107 (55.4%) | 36 (16.7%) | 6.2 | <0.0001 |
| Hs03103056_cn | 3.5 or more | 76 (39.4%) | 22 (10.2%) | 5.7 | <0.0001 |
| Hs03899300_cn | less than 1.5 | 148 (76.7%) | 56 (25.9%) | 9.4 | <0.0001 |
| Hs03908783_cn | less than 0.5 | 46 (23.8%) | 22 (10.2%) | 2.8 | 0.0003 |
| Hs03898338_cn | less than 1.5 | 161 (83.4%) | 64 (29.6%) | 11.9 | <0.0001 |
| Hs04093415_cn | 9.0 or more | 8 (4.1%) | 0 (0.0%) | 19.6 | 0.0023 |
| Hs04090898_cn | 12.0 or more | 7 (3.6%) | 0 (0.0%) | 17.4 | 0.0049 |

TABLE 8

| | Hs06535529_cn | Hs03103056_cn | Hs03899300_cn | Hs03908783_cn | Hs03898338_cn | Hs04093415_cn | Hs04090898_cn |
| --- | --- | --- | --- | --- | --- | --- | --- |
| Hs06535529_cn | | | | | | | |
| Hs03103056_cn | 75.1<br>66.7 | | | | | | |
| Hs03899300_cn | 73.6<br>75.5 | 79.3<br>75.0 | | | | | |
| Hs03908783_cn | 79.8<br>55.1 | 71.0<br>66.7 | 83.4<br>81.0 | | | | |
| Hs03898338_cn | 78.8<br>75.0 | 81.4<br>74.1 | 79.8<br>75.9 | 84.5<br>75.5 | | | |
| Hs04093415_cn | 82.4<br>51.9 | 61.1<br>52.3 | 76.2<br>74.5 | 71.5<br>60.2 | 78.8<br>75.0 | | |
| Hs04090898_cn | 81.8<br>51.4 | 60.6<br>53.2 | 75.7<br>74.5 | 72.0<br>60.2 | 78.8<br>75.0 | 18.1<br>85.2 | |

The upper and lower columns each indicate sensitivity (%) and specificity (%), respectively.

The invention claimed is:

1. A method for determining that a human subject is highly susceptible to breast cancer, comprising the following steps:
   1) contacting a nucleic acid sample from a human subject with a first probe consisting of SEQ ID NO: 3 and a second probe consisting of SEQ ID NO: 4 to form hybridization complexes between the first and second probes and target nucleic acids in the sample;
   2) determining the quantity of the hybridization complexes;

3) detecting a decrease in the DNA copy number of a first human chromosomal region in 15q26.3 consisting of the nucleotide sequence shown in SEQ ID NO: 3, and a second human chromosomal region in 15q26.3 consisting of the nucleotide sequence shown in SEQ ID NO: 4 based on the quantity of the hybridization complexes determined in step 2);

4) comparing the decrease in DNA copy number of the two human chromosomal regions of the human subject detected in step 3) to the DNA copy number of the two human chromosomal regions in an individual without breast cancer; and 5) determining that the human subject is highly susceptible to breast cancer based on the determination of a frequency of DNA copy number of less than 1.5 of the nucleotide sequence shown in SEQ ID NO: 3, and a frequency of DNA copy number of less than 0.5 of the nucleotide sequence shown in SEQ ID NO: 4.

2. The method of claim 1, wherein the quantity of hybridization complexes of step 2) is determined by a polymerase chain reaction (PCR).

\* \* \* \* \*

```
                          SEQUENCE LISTING

<160> NUMBER OF SEQ ID NOS: 8

<210> SEQ ID NO 1
<211> LENGTH: 82
<212> TYPE: DNA
<213> ORGANISM: Homo sapiens

<400> SEQUENCE: 1
tcgctgtgcc tgatttcaga gccggtttct gcggtaaact catggcaaag cgaagccacc      60
aaccccccca gagcgggacc gg                                               82

<210> SEQ ID NO 2
<211> LENGTH: 116
<212> TYPE: DNA
<213> ORGANISM: Homo sapiens

<400> SEQUENCE: 2
tggcaacatc tcaatatccr cagaattttc atatttatcc aggtagaatt gataaacaga      60
aaattccaca agaaccataa attatttaac acatacacac acacactcaa atttag         116
```

```
<210> SEQ ID NO 3
<211> LENGTH: 106
<212> TYPE: DNA
<213> ORGANISM: Homo sapiens

<400> SEQUENCE: 3
actgcctggc actaaggttt agagttatga gtcggtgctt ccctgtcact tcacttaacc    60
ctctgagtgt gcagtttgta gatttgttaa ctgcactgag aggtcc                  106

<210> SEQ ID NO 4
<211> LENGTH: 97
<212> TYPE: DNA
<213> ORGANISM: Homo sapiens

<400> SEQUENCE: 4
gcctgcctcc crgcatgggc cgcggcctcc gccatgggct ccgtgcggtg gtttctcggg    60
tacacgctcg tgagccyggc tgatgcgcca catgcct                             97

<210> SEQ ID NO 5
<211> LENGTH: 77
<212> TYPE: DNA
<213> ORGANISM: Homo sapiens

<400> SEQUENCE: 5
atcgctgctg gatctcttct gtcatccctc ccaggaccca ttggtcctac tggcccactt    60
ccagaaagca agccatc                                                   77

<210> SEQ ID NO 6
<211> LENGTH: 75
<212> TYPE: DNA
<213> ORGANISM: Homo sapiens

<400> SEQUENCE: 6
gtgtcgaggc tgctccttaa aygcttcttg cctgcacgct gtgcgtggaa acccaaagaa    60
gtgagagacg cgagg                                                     75

<210> SEQ ID NO 7
<211> LENGTH: 107
<212> TYPE: DNA
<213> ORGANISM: Homo sapiens

<400> SEQUENCE: 7
ctcctagtgg gatcctacaa ctctcagaac aacagggtcc ccctggactg tgagcacagt    60
agaaccagct cttttcttggg attttaagaa aacagacaag cttcgcg                107

<210> SEQ ID NO 8
<211> LENGTH: 87
<212> TYPE: DNA
<213> ORGANISM: Homo sapiens

<400> SEQUENCE: 8
ccctagtctc agaccttccc aagggacatg ggagtggagt gacagracgc actcagctcg    60
tggccccact gatgagcttc cctccgc                                        87
```